US011638659B2

(12) United States Patent
Dijkstra

(10) Patent No.: US 11,638,659 B2
(45) Date of Patent: May 2, 2023

(54) BED FOR THERAPEUTIC AND RECREATIONAL APPLICATIONS

(71) Applicant: Light Tree Ventures Holding B.V., Rijswijk (NL)

(72) Inventor: Alain Dijkstra, Amstelveen (NL)

(*) Notice: Subject to any disclaimer, the term of this patent is extended or adjusted under 35 U.S.C. 154(b) by 492 days.

(21) Appl. No.: 16/816,316

(22) Filed: Mar. 12, 2020

(65) Prior Publication Data

US 2021/0282962 A1 Sep. 16, 2021

(51) Int. Cl.
*A61F 7/08* (2006.01)
*A61N 5/06* (2006.01)
(Continued)

(52) U.S. Cl.
CPC ............... *A61F 7/08* (2013.01); *A61B 5/369* (2021.01); *A61B 5/4836* (2013.01); *A61G 7/05* (2013.01);
(Continued)

(58) Field of Classification Search
CPC ............ A61F 7/08; A61F 2007/0054; A61F 2007/0095; A61F 2007/0059; A61B 5/369; A61B 5/4836; A61B 18/12; A61G 7/05; A61G 2210/90; A61G 7/012; A61G 7/015; A61G 13/08; A61N 5/0625; A61N 2005/0626; A61N 2005/0652; A61N 2005/0653; A61N 2005/0659; A61M 25/02
See application file for complete search history.

(56) References Cited

U.S. PATENT DOCUMENTS 5,304,112 A  4/1994 Mrklas
6,899,725 B2 5/2005 Lee
(Continued)

FOREIGN PATENT DOCUMENTS

DE  202013102477 U1 * 8/2013 ........... A47C 21/048

OTHER PUBLICATIONS

SPA equipment Vichy shower water shower massage bed with led light therapy, https://www.alibaba.com/product-detail/SPA-equipment-vichy-shower-water-shower_60572131410.html.
(Continued)

*Primary Examiner* — Carl H Layno
*Assistant Examiner* — Aya Ziad Bakkar
(74) *Attorney, Agent, or Firm* — Willie Jacques; Emanus, LLC

(57) ABSTRACT

A bed for therapeutic and recreational applications, comprises a frame structure, a mattress provided on the frame structure of the bed, a plurality of Light Emitting Diodes (LEDs) configured to emit electromagnetic radiation, an infrared heater assembly provided within the frame structure, the infrared heater assembly including a plurality of flexible heating elements connected with a power source, a plurality of temperature sensors provided at a plurality of locations on the frame structure and the mattress in order to generate signals in correlation with temperature values at the plurality of locations. Further, the frame structure includes a plurality of frame segments adapted to rotate to respective predetermined angles. Also, the mattress is made from at least partially transparent material and includes a fluid that is at least partially transparent.

19 Claims, 12 Drawing Sheets

(51) Int. Cl.
    *A61B 5/00*         (2006.01)
    *A61G 7/05*         (2006.01)
    *A61B 5/369*       (2021.01)
    *A61F 7/00*         (2006.01)

(52) U.S. Cl.
    CPC .... *A61N 5/0625* (2013.01); *A61F 2007/0054* (2013.01); *A61F 2007/0095* (2013.01); *A61G 2210/90* (2013.01); *A61N 2005/0626* (2013.01); *A61N 2005/0652* (2013.01); *A61N 2005/0653* (2013.01); *A61N 2005/0659* (2013.01)

(56) References Cited

U.S. PATENT DOCUMENTS

| | | | |
|---|---|---|---|
| 7,328,708 | B2 | 2/2008 | Malak |
| 7,503,926 | B2 | 3/2009 | Daffer et al. |
| 8,444,558 | B2 | 5/2013 | Young et al. |
| 8,672,842 | B2 | 3/2014 | Kenalty et al. |
| 9,005,101 | B1 | 4/2015 | Van Erlach |
| 9,549,705 | B2 | 1/2017 | Riley et al. |
| 10,163,321 | B2 | 12/2018 | Furuland |
| 2008/0120784 | A1 | 5/2008 | Warner et al. |
| 2010/0191158 | A1 | 7/2010 | Damron et al. |
| 2012/0016274 | A1* | 1/2012 | Howe ............ A61M 21/02 601/148 |
| 2013/0197375 | A1 | 8/2013 | Heise et al. |
| 2013/0211208 | A1 | 8/2013 | Varadan et al. |
| 2015/0283400 | A1 | 10/2015 | Hatley |
| 2016/0012747 | A1 | 1/2016 | Garrues Remirez |
| 2017/0053068 | A1 | 2/2017 | Pillai et al. |
| 2017/0202363 | A1* | 7/2017 | Kim ............ A47C 27/10 |
| 2018/0110960 | A1 | 4/2018 | Youngblood et al. |

OTHER PUBLICATIONS

A $30,000 Waterbed That Vibrates With Music, https://www.wired.com/2014/02/tranquility-pod/.
Smart cot, https://www.smart-cot.com/.
Water therapy spa bed, https://www.thisiswhyimbroke.com/water-and-light-therapy-spa-bed/.
Prosun massage bed https://prosun.com/wellness/aquafrixio-hydro-massage-bed/.

\* cited by examiner

BED FOR THERAPEUTIC AND RECREATIONAL APPLICATIONS

TECHNICAL FIELD

The present invention relates generally to recreational and therapeutic irradiation and heating apparatus. More specifically, the present invention relates to a bed to be used as a medium for providing the irradiation and the heating for therapeutic and recreational applications.

BACKGROUND ART

Sauna beds and pods for recreational and therapeutic use are readily available in markets. Further, much research has been performed affirming the physiological benefits of the sauna beds and the pods. However, products available in the art in the form of sauna beds, pods or variations thereof, are limited in their applications. In that regard, most of the products use infrared radiation in far infrared end of the electromagnetic spectrum to achieve heating of the body of a person using such products. Primarily, Light Emitting Diodes (LEDs) are used as sources for generating far infrared radiation to achieve the heating effect. However, such products are incapable of providing additionally regulated and specifically targeted benefits, though residual benefits in form of skin repair and pain relief have been recorded in some cases. In that regard, some of the solutions have been suggested in the state of the art.

U.S. Pat. No. 7,503,926B2 discloses a personal therapy or sauna compartment formed with a base, having the interior of the base in which a person can lie. A cover is provided over the base and covers the body of a person lying in the bed, with the head of the person outside of the cover. The bed is supported above massage showerheads that provide massage water impingement upwardly against the back of the person on the bed. Infrared heaters are placed in the cover, and showerheads in the cover provide for comfort and showering the person lying on the bed. Also, light support panels include multi-colored LED lights that will provide for a light projection rearwardly toward the head of the user that is lying on the pad or mattress. The lights thus can be directly viewed and they will provide reflected light. However, the disclosed compartment is limited by its complexity of construction and resultant costs of manufacturing. Moreover, many of the mechanisms described, such as the impingement of water would require a relatively large amount of power consumption.

U.S. Pat. No. 9,005,101B1 discloses a system and method for delivering a specified therapy to body portions based on the sensed biological parameters. The patent document discloses a substrate having a plurality of pressure or thermal sensors that detect an accurate position of a human being laying on a substrate (bed, mattress, etc.). It also comprises several sensors that sense biological parameters (temperature, acceleration, moisture or sweat parameters, resistance, stress level, heart rate, respiration rate, brain waves, blood flow rate, metabolic activity, blood oxygenation, etc.) of the human being laying on the bed. Based on the feedback of biological parameters of human being laying on the bed, the therapy devices associated with the substrate are configured to deliver desired therapies. However, the disclosed system is again limited by the complexity of control architecture and is rather silent on how specifically the control architecture achieves the intended functions. Moreover, the document does not sufficiently disclose constructional structures to support the control architecture and how the several electronic components will be packaged for convenient use by a user.

US20180110960A1 discloses a system and method for stress reduction and sleep promotion by adjusting the temperature of the mattress pad surface using a fluid system. It comprises a plurality of body sensors (respiration sensor, electrooculography sensor, heart rate sensor, bodyweight sensor, electromyography sensor, brain wave sensor, temperature sensor, analyte sensor, pulse oximeter sensor, blood pressure sensor, electrodermal activity sensor, and body weight sensor) that senses the various parameter of human being laying on the bed. It helps in predicting the values for the stress reduction and sleep promotion system. The system also comprises a red light or infra-red light emitting device to provide therapy. However, heating of the mattress is being achieved through the cycling of a working fluid, therefore requiring relatively bulky and complex hydraulic or pneumatic systems and significantly high electricity consumption.

All of the solutions discussed above disclose either insufficient mechanical constructional details or relatively complex and cost-intensive solutions. In that regard, it is unlikely, that with the cost and the complexity involved, the aforementioned solutions would be easy for adoption by an average consumer, and would rather require commercial resources, large customized spaces and skilled professionals to operate them.

Therefore, there is a need in the art for a bed for recreational and therapeutic purposes that does not suffer from the aforementioned deficiencies.

SUMMARY OF THE INVENTION

According to a first aspect of the present invention, there is provided a bed for therapeutic and recreational applications, the bed comprising a frame structure, a mattress provided on the frame structure of the bed, a plurality of Light Emitting Diodes (LEDs) configured to emit electromagnetic radiation, an infrared heater assembly provided within the frame structure, the infrared heater assembly including a plurality of flexible heating elements connected with a power source, a plurality of temperature sensors provided at a plurality of locations on the frame structure and the mattress in order to generate signals in correlation with temperature values at the plurality of locations, wherein the frame structure includes a plurality of frame segments adapted to rotate to respective predetermined angles, in order to lift or recline, with respect to a locating surface on which the bed has been located, the rotation of the plurality of frame segments being achieved through one or more actuators and wherein the mattress is made from at least partially transparent material and includes a fluid that is at least partially transparent.

In an alternative embodiment of the invention, the mattress includes a foam layer made from a Shape Memory Polymer (SMP).

In an alternative embodiment of the invention, the frame structure includes an upper panel, the upper panel being at least partially transparent, the mattress being provided on the upper panel of the frame structure, wherein the plurality of LEDs have been provided on a second surface at a predetermined depth from the upper panel, and wherein the plurality of flexible heating elements are provided along the second surface.

In an alternative embodiment of the invention, the plurality of LEDs are located inside the mattress.

In an alternative embodiment of the invention, the plurality of flexible heating elements are provided within the mattress and are adapted to align with superficial veins of a body of a user.

In an alternative embodiment of the invention, the plurality of flexible heating elements have been located in a plurality of respective grooves in a fabric of the mattress and a predetermined amount of clearance has been provided in the plurality of grooves, to allow for the adjustment of the plurality of flexible heating elements.

In an alternative embodiment of the invention, each one of the plurality of LEDs further comprises a focusing lens configured to confine the emitted electromagnetic radiation within a beam angle within 30 degrees to 60 degrees.

In an alternative embodiment of the invention, the bed further comprises a plurality of auxiliary sensors configured to obtain a plurality of auxiliary measurements.

In an alternative embodiment of the invention, the plurality of auxiliary sensors include an Electro-Encephalogram (EEG) unit.

In an alternative embodiment of the invention, the bed further comprises a reservoir, wherein the mattress includes a plurality of pressure-activated valves that allow a quantity of the fluid to be transferred to the reservoir when pressure is applied on a top surface of the mattress and allow the transferred quantity to be returned to the mattress when the pressure is released.

In an alternative embodiment of the invention, the reservoir is provided in one or more locations including within the frame structure and attached with the mattress.

In an alternative embodiment of the invention, the bed further comprises a pump unit, wherein the pump unit is configured to facilitate the transfer of the quantity of the fluid from the mattress to the reservoir and the return of the quantity of the fluid from the reservoir to the mattress.

In an alternative embodiment of the invention, the pump unit is provided within one or more of the frame structure and the mattress.

In an alternative embodiment of the invention, the mattress has been provided with predetermined fluid flow channels in order to allow the fluid pressurized by the pump unit, to circulate within the mattress, in a predetermined pattern.

In an alternative embodiment of the invention, the predetermined fluid flow channels include a plurality of baffles that are adjustable in order to modify the predetermined fluid flow channels.

In an alternative embodiment of the invention, the plurality of LEDs are configured to emit electromagnetic radiations in one or more of red light frequency range and infrared frequency range of the electromagnetic spectrum.

In an alternative embodiment of the invention, the plurality of LEDs are configured to emit electromagnetic radiations in one or more frequencies of visible light frequency range of the electromagnetic spectrum.

In an alternative embodiment of the invention, the bed further comprises a heat sink configured to receive heat energy generated by the plurality of LEDs.

In an alternative embodiment of the invention, the bed further comprises a fan assembly configured to enhance dissipation of the heat received by the heat sink, through forced or induced draft of air.

In an alternative embodiment of the invention, the plurality of LEDs have been mounted on a mounting structure using Surface Mount Technology (SMT).

In an alternative embodiment of the invention, the plurality of LEDs are provided on one or more of flexible Organic LED (OLED) and inorganic LED based panels.

In an alternative embodiment of the invention, a frame segment of the frame structure includes a plurality of discrete longitudinal structures, wherein the plurality of longitudinal structures include a plurality of respective slats, the plurality of LEDs being divided amongst the plurality of slats and wherein the mattress has been divided into a plurality of mattress segments provided within the plurality of respective longitudinal structures, the plurality of mattress segments provided on the plurality of respective slats.

In an alternative embodiment of the invention, the fluid is selected from a group comprising water, a gel, and combinations thereof.

In an alternative embodiment of the invention, the bed further comprises a processor and a memory unit, the memory unit comprising machine-readable instructions, the machine-readable instructions when executed by the processor, enables the processor to receive the signals from the plurality of temperature sensors and a plurality of auxiliary sensors, determine the temperature values from the signals received from the plurality of temperature sensors, regulate electrical power being supplied to the infrared heater and the plurality of LEDs in correlation with the determined temperature values, regulate emission characteristics of the electromagnetic radiation emitted by the plurality of LEDs and regulate electrical power being supplied to the one or more actuators in order to enable rotation of the plurality of frame segments.

In an alternative embodiment of the invention, the bed further comprises a communication unit capable of communicating with a computing device through one or more of a short range and a long range communication network, wherein the processor is further enabled to receive a control input from the computing device, modify the one or more of the emission characteristics of the electromagnetic radiation and heat generated by the infrared heater, in correlation with the received control input.

In an alternative embodiment of the invention, the computing device is a remote control for the bed.

In an alternative embodiment of the invention, the processor is further enabled to execute a media file in correlation with the control input.

In an alternative embodiment of the invention, the processor is further enabled to execute a media file in correlation with signals provided by a plurality of auxiliary sensors.

In an alternative embodiment of the invention, the bed further comprises a fastening arrangement capable of holding the computing device.

According to a second aspect of the present invention, there is provided a frame structure of a bed for therapeutic and recreational applications, the frame structure comprising a plurality of Light Emitting Diodes provided within the frame structure and configured to emit electromagnetic radiation, an infrared heater assembly provided within the frame structure, the infrared heater assembly including a plurality of flexible heating elements connected with a power source, a plurality of temperature sensors provided at a plurality of locations on the frame structure, wherein the frame structure includes a plurality of frame segments adapted to rotate to respective predetermined angles in order to lift or recline the plurality of frame segments with respect to a locating surface on which the bed has been located, the rotation of the plurality of frame segments being achieved through one or more actuators.

In an alternative embodiment of the invention, a frame segment of the frame structure includes a plurality of discrete longitudinal structures, wherein the plurality of longitudinal structures include a plurality of respective slats, the plurality of LEDs being divided amongst the plurality of slats and wherein the mattress has been divided into a plurality of mattress segments provided within the plurality of respective longitudinal structures, the plurality of mattress segments provided on the plurality of respective slats.

According to a third aspect of the present invention, there is provided a method for utilizing a bed for therapeutic and recreational applications, the bed comprising a frame structure, a mattress provided on the frame structure of the bed, a plurality of Light Emitting Diodes configured to emit electromagnetic radiation, an infrared heater assembly provided within the frame structure, the infrared heater assembly including a plurality of flexible heating elements connected with a power source, a plurality of temperature sensors provided at a plurality of locations on the frame structure and the mattress in order to generate signals in correlation with temperature values at the plurality of locations, wherein the frame structure includes a plurality of frame segments adapted to rotate to respective predetermined angles in order to lift or recline the plurality of frame segments with respect to a locating surface on which the bed has been located, the rotation of the plurality of frame segments being achieved through one or more actuators and wherein the mattress is made from at least partially transparent material and includes a fluid that is at least partially transparent. The method comprises steps of regulating electrical power being supplied to the one or more actuators in order to enable rotation of the plurality of frame segments, receiving the signals from the plurality of temperature sensors, determining the temperature values from the signals received from the plurality of temperature sensors, regulating electrical power being supplied to the infrared heater and the plurality of LEDs in correlation with the determined temperature values and regulating emission characteristics of the electromagnetic radiation emitted by the plurality of LEDs.

In the context of the specification, a "polymer" is a material made up of long chains of organic molecules (having eight or more organic molecules) including, but not limited to, carbon, nitrogen, oxygen, and hydrogen as their constituent elements. The term polymer is envisaged to include both naturally occurring polymers such as wool, and synthetic polymers such as polyethylene and nylon.

In the context of the specification, "Shape Memory Polymers (SMPs)" are synthetic polymers that are capable of deforming into a non-equilibrium shape under compression, wherein elastic stresses are frozen into the material structure. Additionally, the SMPs are capable of returning to their original shape that existed before deformation (also known as equilibrium shape) in response to an external stimulus known as a trigger. Commonly known triggers include temperature, electricity, pH, ionic strength and light. SMPs may be fabricated into a number of forms such as sheets, bulks, fibers, and foams. The most commonly used materials include Polyurethane and derivatives of Polyurethane, however, in some cases, other materials, such as Polyethylene-Terephthalate (PET) have also been utilized to generate the SMPs.

BRIEF DESCRIPTION OF ACCOMPANYING DRAWINGS

So that the manner in which the above-recited features of the present invention can be understood in detail, a more particular description of the invention, briefly summarized above, may have been referred by embodiments, some of which are illustrated in the appended drawings. It is to be noted, however, that the appended drawings illustrate only typical embodiments of this invention and are therefore not to be considered limiting of its scope, for the invention may admit to other equally effective embodiments.

These and other features, benefits, and advantages of the present invention will become apparent by reference to the following text figure, with like reference numbers referring to like structures across the views, wherein.

DETAILED DESCRIPTION

Figure 1A:
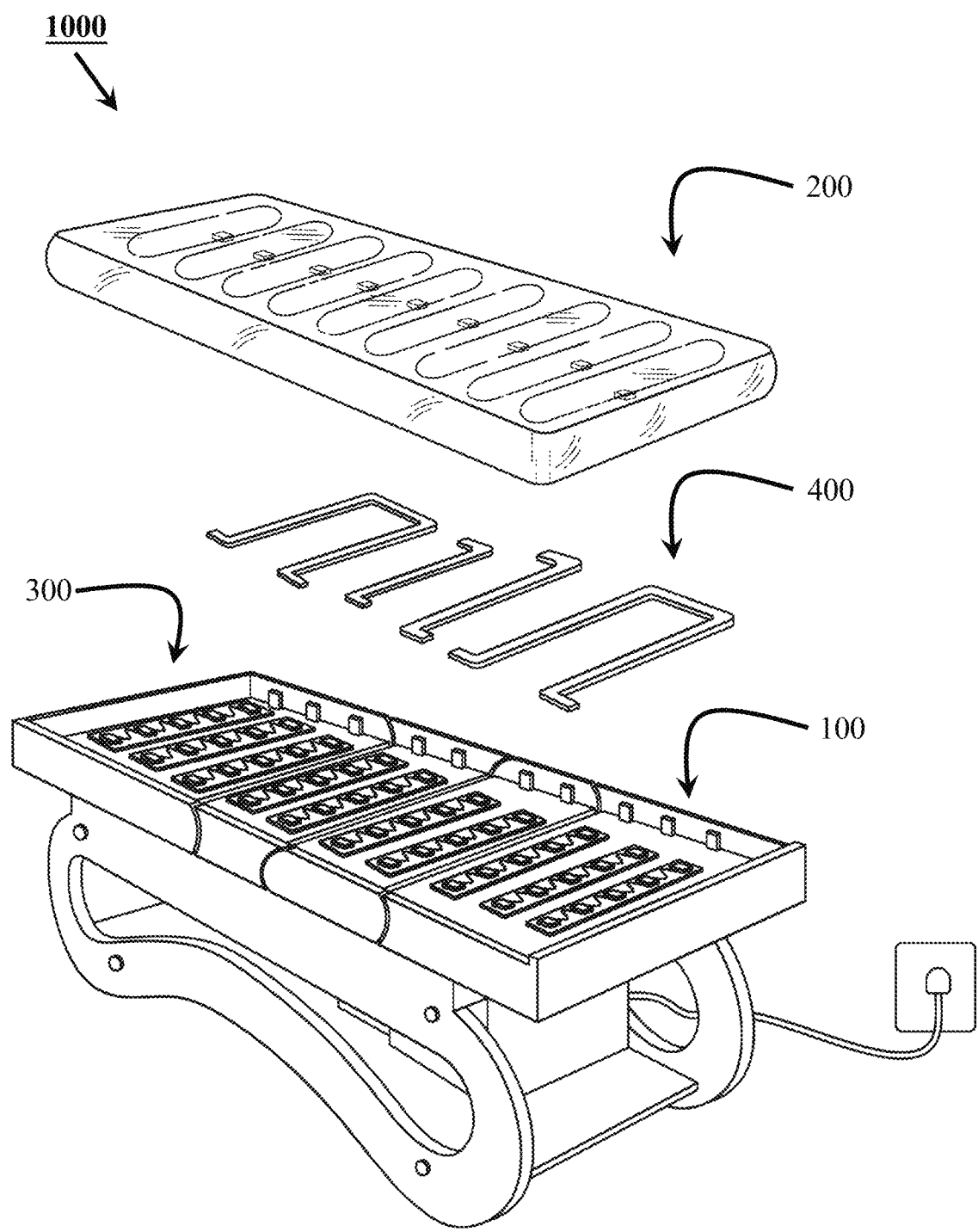
FIG. 1A illustrates an exploded view of a bed for therapeutic and recreational applications, in accordance with an embodiment of the present invention.

While the present invention is described herein by way of example using embodiments and illustrative drawings, those skilled in the art will recognize that the invention is not limited to the embodiments of drawing or drawings described, and are not intended to represent the scale of the various components. Further, some components that may form a part of the invention may not be illustrated in certain figures, for ease of illustration, and such omissions do not limit the embodiments outlined in any way. It should be understood that the drawings and detailed description thereto are not intended to limit the invention to the particular form disclosed, but on the contrary, the invention is to cover all modifications, equivalents, and alternatives falling within the scope of the present invention as defined by the appended claims. As used throughout this description, the word "may" is used in a permissive sense (i.e. meaning having the potential to), rather than the mandatory sense, (i.e. meaning must). Further, the words "a" or "an" mean "at least one" and the word "plurality" means "one or more" unless otherwise mentioned. Furthermore, the terminology and phraseology used herein is solely used for descriptive purposes and should not be construed as limiting in scope. Language such as "including," "comprising," "having," "containing," or "involving," and variations thereof, is intended to be broad and encompass the subject matter listed thereafter, equivalents, and additional subject matter not recited, and is not intended to exclude other additives, components, integers or steps. Likewise, the term "comprising" is considered synonymous with the terms "including" or "containing" for applicable legal purposes. Any discussion of documents acts, materials, devices, articles and the like is included in the specification solely for the purpose of providing a context for the present invention. It is not suggested or represented that any or all of these matters form part of the prior art base or were common general knowledge in the field relevant to the present invention.

In this disclosure, whenever a composition or an element or a group of elements is preceded with the transitional phrase "comprising", it is understood that we also contemplate the same composition, element or group of elements with transitional phrases "consisting of", "consisting", "selected from the group of consisting of, "including", or "is" preceding the recitation of the composition, element or group of elements and vice versa.

The present invention is described hereinafter by various embodiments with reference to the accompanying drawings, wherein reference numerals used in the accompanying drawing correspond to the like elements throughout the description. This invention may, however, be embodied in many different forms and should not be construed as limited to the embodiment set forth herein. Rather, the embodiment is provided so that this disclosure will be thorough and complete and will fully convey the scope of the invention to those skilled in the art. In the following detailed description, numeric values and ranges are provided for various aspects of the implementations described. These values and ranges are to be treated as examples only and are not intended to limit the scope of the claims. In addition, a number of materials are identified as suitable for various facets of the implementations. These materials are to be treated as exemplary and are not intended to limit the scope of the invention.

It is envisaged that a bed for recreational and therapeutic purposes, be provided, that is capable of providing at least irradiation and heat based therapies. In that regard, the bed may be provided with several Light Emitting Diodes (LEDs) for irradiation in several frequency ranges of the electromagnetic spectrum. Additionally, several heating elements (that are flexible or pliable for design and packaging purposes) may also be provided for providing heating through irradiation of infrared wavelengths. However, in order to regulate temperature at several locations of the bed, a number of temperature sensors may be installed at such locations. In that regard, maintenance of regulated temperatures in areas directly in contact with a body of a user, power electronic circuitry and thermally fusible surfaces may be essential for the longevity of the bed. The bed is also envisaged to be customizable for several body and therapy types. In that regard, a frame structure of the bed may be made from combining several frame segments that may be mutually adjustable through rotation and sliding for adapting to several body postures and sizes. The construction of frame structure is not limited to one or two constructions and again may vary to further enhance certain specific features of the invention. For example, one or more frame segments of the frame structure may be divided into a number of slats, where the mattress has been equally segmented and integrated with the slats of the frame structure.

To provide sufficient cushioning during usage, a mattress is also envisaged to be provided over the frame structure. The mattress is further envisaged to be at least partially transparent to allow for the LED irradiation to pass through and be capable of conducting heat. Also, it is envisaged to be filled with a fluid that may be a Newtonian or a Non-Newtonian fluid as per specific application. The fluid in that regard may be a liquid such as water or shear-thinning fluid such as a gel of a predetermined composition or combinations thereof. It is natural that the fluid in itself may also be at least partially transparent and capable of conducting heat. In order to enhance comfort, the mattress may be designed to deform in a manner capable of snugly accommodating the body of the user. In that regard, the mattress may be provided with pressure actuated valves that may sense the pressure exerted by the body of the user, and allow a portion of the fluid to be transferred to an external reservoir to allow for the deformation of the mattress. In applications, where the fluid is too viscous to flow on its own or just to enhance the response time of the mattress during the deformation and subsequent reformation, a pump may be used to facilitate the flow of the fluid. However, mechanisms using gravity feeding and siphoning phenomenon may also be used to at least partially aid the pump assisted fluid flow. Additionally, shape memory foams may also be used in certain applications to enhance the cushioning effect.

While the LEDs may be provided within the frame structure under a transparent protective sheet or panel, sealed LEDs may also be used for placement within the mattress. In any case, it would be preferable to install the LEDs, through Surface Mount Technology (SMT). Although, such an installation is not binding for working of the invention, and the installation methodology may vary depending upon cost and manufacturing constraints and any developments appearing in the foreseeable future. Additionally, one or more lenses and phosphor coatings may also be used in addition to the LEDs, to regulate several illumination parameters such as beam angle, color, and intensity, etc. In addition to the temperature sensors, several auxiliary sensors such as pulse rate sensor, breath rate sensor, IR transceivers, angle sensor (encoders), Electro-Encephalogram (EEG) may also be provided in the bed for monitoring several other parameters pertaining to the user and functioning of the bed during usage, as will be presented in later discussion. Additionally, the LED irradiation may be varied as per the requisite application. For example, while red and infrared bands are well documented for their therapeutic characteristics, there have been sufficient clinical studies on the effects of other colored radiations as well, such as yellow, blue and green, etc. Moreover, the use of colored lighting has also been documented for different therapeutic applications, as traditional knowledge in several cultures such as Yoga in India. However, LEDs do have a tendency to generate residual heat, especially at p-n junctions, that needs to be dissipated in order to regulate the temperature of the bed and ensure efficiency and longevity of the LEDs. In that regard, heat sinks of varying constructions may be provided based on factors such as the number of LEDs, kind of applications, packaging constraints, electrical power being consumed, the efficiency of LEDs and the amount of heat generated, etc.

In addition, it is envisaged that the bed may be controlled using an external computing device such as a smartphone, Personal Digital Assistant (PDA), a tablet or even a remote control, that may be connected with the bed through a wired or wireless connection. In that regard, the bed is envisaged to be provided with a control architecture that includes a processor (such as a general purpose processor, a Field Programmable Gate Array (FPGA), an Application Specific Integrated Circuit (ASIC) or the like), volatile and non-volatile memory units, op-amps, amplifiers, rectifiers, inverters, and other circuit components. The non-volatile memory is envisaged to be capable of storing machine readable instructions that may be written in a well-known computing language such as C, C++, and Python, etc. The processor, on the execution of such machine readable instructions may cause several onboard systems to operate, such as during rotation and translation of frame segments, control of heating, regulation of heat dissipation through heat sinks, wavelength or frequency control of electromagnetic radiation and the like. The processor may also allow the computing device to communicate with the bed through a communication interface, that may be wired or wireless, in order to receive a control signal from the computing device. In that regard, the processor may be able to modify the one or more of the emission characteristics of the electromagnetic radiation and the heat generated by the infrared heater, in correlation with the received control input. Referring to the figures now, the invention will be explained in further detail.

Figure 1B:
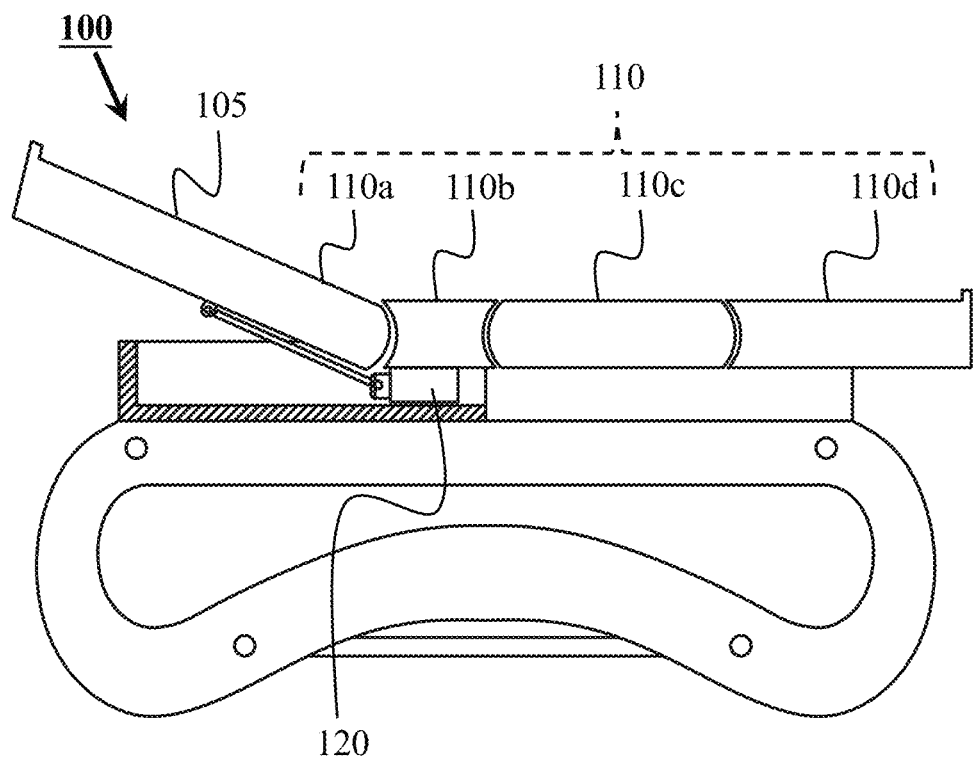
FIGS. 1B and 1C illustrate a frame structure of the bed illustrated in FIG. 1A, depicted in two exemplary arrangements of utilization.
Figure 1C:
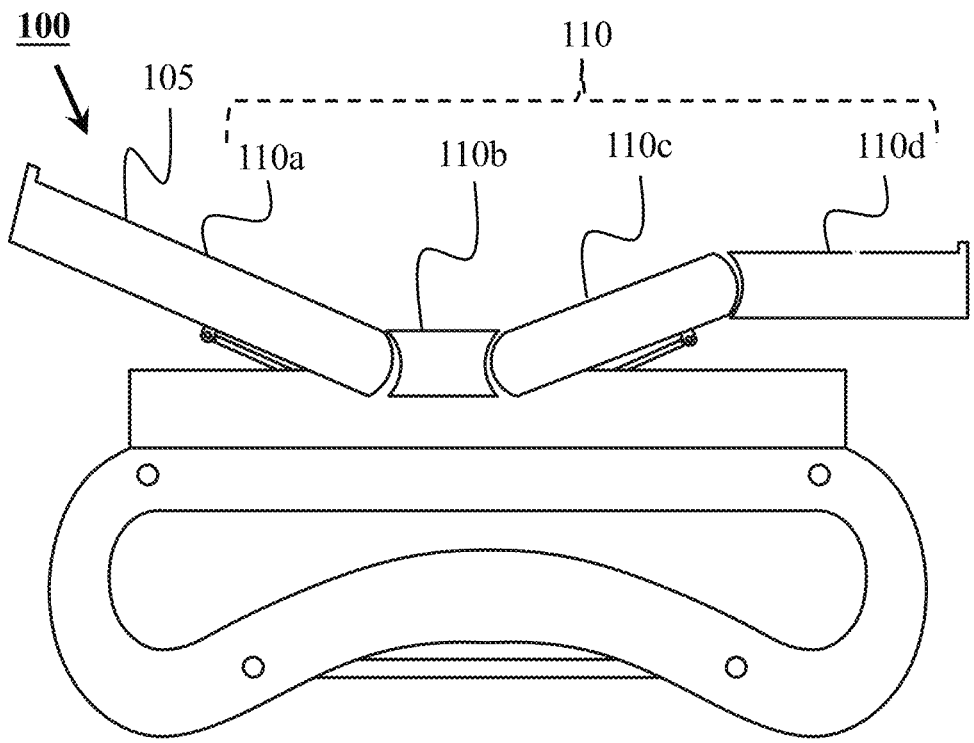

FIG. 1A illustrates an exploded view of a bed 1000 for therapeutic and recreational applications, in accordance with an embodiment of the present invention. As can be seen from FIG. 1A, the bed 1000 includes a frame structure 100, a mattress 200 and an infrared heater 400. The mattress 200 is supposed to be located over the frame structure 100. FIGS. 1B and 1C illustrate the frame structure 100 of the bed 1000 of FIG. 1A, depicted in two exemplary arrangements of utilization. It is further envisaged that the frame structure 100 includes a plurality of frame segments 110 (110a, 110b, 110c, and 110d) adapted to rotate to respective predetermined angles. The rotation of the plurality of frame segments 110, with respect to each other allows the plurality of frame segments 110 to lift or recline, with respect to a locating surface on which the bed 1000 has been located. For example, the bed 1000 may be removably fastened to a floor surface through the use of fasteners such as studs and bolts. Alternately, the bed 1000 or the frame structure 100 includes a plurality of casters in order to allow the bed 1000 to be movable.

As illustrated in FIG. 1B, the depicted arrangement of the frame structure 100 would enable the user to be in position where the spine of the user is rested against a frame segment 110a that is in reclining position. Such an arrangement would allow the user to spend a fair amount of time on the bed 1000, without straining their spine and the user would still be able to perform routine tasks such as checking their messages or reading a book. In the arrangement depicted in FIG. 1C, however, the frame segment 110a is in a reclining position, and frame segments 110c and 110d are arranged to lift the legs of the user. In such a position, the spine of the user will be even more relaxed and blood flow to upper portions of the body of the user will also be enhanced. Moreover, muscle tissues in the legs of the user will also be comparatively relaxed and less strained.

In several alternative embodiments, the plurality of frame segments 110 may also be allowed for linear translation with respect to each other in order to accommodate several body sizes. The rotation or translation of the plurality of frame segments 110 may be achieved through one or more actuators 120. In that regard, the one or more actuators 120 may include electrical actuators such as Alternating Current (AC) motors, Direct Current (DC) motors, Linear Electromagnetic Motors (LEM) and the like. Additional gears and links may be provided for torque multiplication, power transmission and conversion of rotational motion of the AC and DC motors to linear motion of the plurality of frame segments 110 during usage. In several alternative embodiments, the one or more actuators 120 may include valve controlled movement of hydraulic and pneumatic fluids.

The mattress 200 however, is envisaged to be made from a synthetic material that is at least partially transparent to electromagnetic radiation at least within Violet light to infrared band of the electromagnetic frequency spectrum. Such synthetic materials may include, but are not limited to, polyester, polyamide, polyaramid, polytetrafluorethylene, polyethylene, polypropylene, polyurethane, silicone, mixtures of polyurethane and polyethyleneglycol, ultrahigh molecular weight polyethylene, high-performance polyethylene, nylon, and LYCRA (also known as Elastane in certain jurisdictions).

It is further envisaged that the mattress 200 be filled with fluid. The fluid again is envisaged to be at least partially transparent to the electromagnetic radiation. In several embodiments, the fluid may be a pure substance or a mixture such as an emulsion, a colloid or a suspension, etc. Such mixtures may be water based or may be based on some organic solvents such as alcohols, aldehydes, fatty acids, and ethers. In several other embodiments, the fluid may be a gel of a predetermined composition depending upon specific application of the bed 1000. It is further envisaged that, at least for certain applications, the mattress 200 be shape compliant. In other words, the mattress 200 should be able to deform to snugly accommodate a body of a user during usage. In that regard, the material of the mattress 200 may be stretchable in order to expand and contract under the weight of the user. Additionally, it is further envisaged that as the total volume of the mattress 200 changes, i.e. reduces during contraction and returns to original value during expansion, the amount of fluid 220 within the mattress 200 be varied accordingly.

Figure 1D:
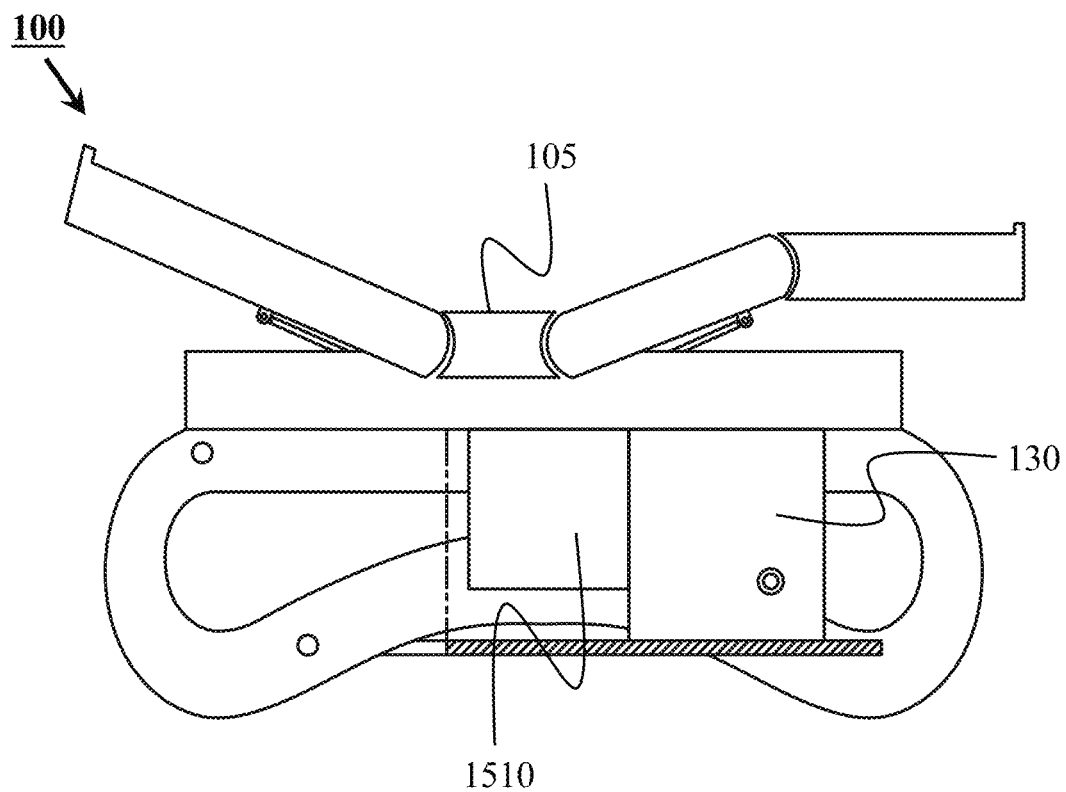
FIG. 1D illustrates a partial sectional view of the frame structure of the bed illustrated in FIG. 1A.
Figure 1E:
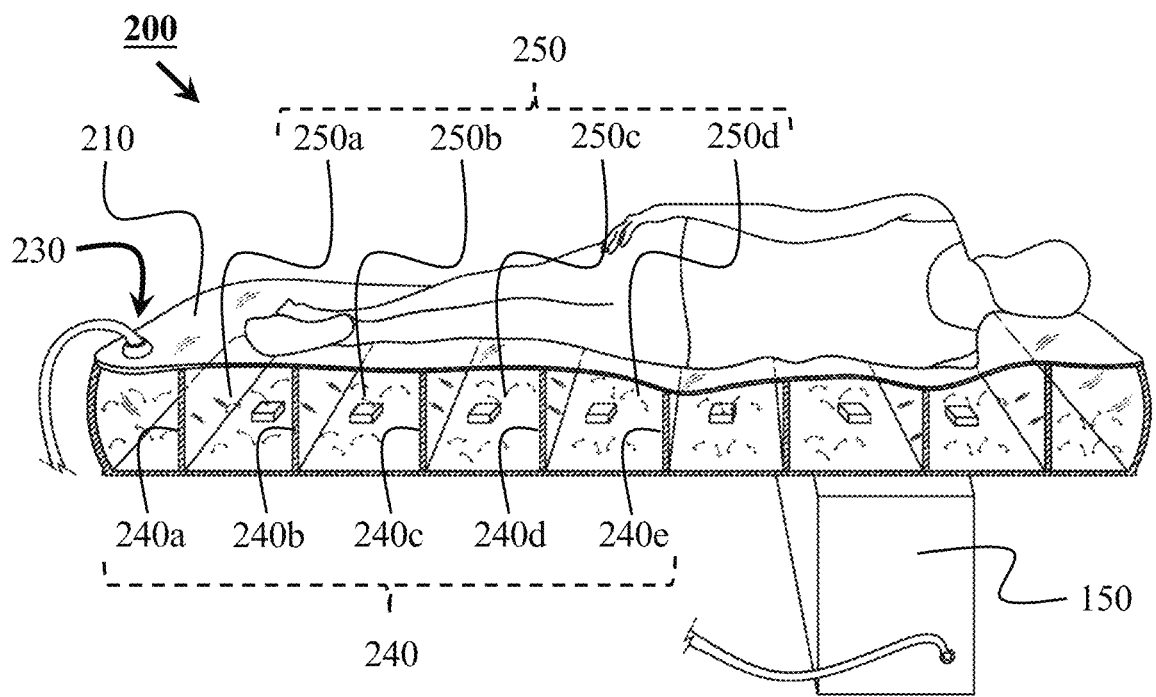
FIG. 1E illustrates a sectional view of a mattress for the bed illustrated in FIG. 1A.

FIG. 1D illustrates a partial sectional view of the frame structure 100 of the bed 1000 illustrated in FIG. 1A. FIG. 1E illustrates a sectional view of a mattress for the bed 1000 illustrated in FIG. 1A. The frame structure 100 has been provided with a reservoir 130 and the mattress 200 has been provided with a plurality of pressure actuated valves 230. The reservoir 130 in that regard may be located at a number of locations within the bed 1000. For example, in certain embodiments, the reservoir 130 may be provided within the frame structure 100 either internally or attached to an outer surface. However, in several alternate embodiments, the reservoir 130 may be attached with the mattress 200.

The plurality of pressure actuated valves 230 allow a quantity of the fluid to be transferred to the reservoir 130 when pressure is applied on a top layer 210 of the mattress 200 and allow the transferred quantity to be returned to the mattress 200 when the pressure is released. In that regard, the plurality of pressure actuated valves 230 may be actuated by sensing a change in hydrostatic pressure of the fluid within the mattress 200 as the user rests on the mattress 200. Alternately, the top layer 210 of the mattress 200 may be provided with pressure transducers or force sensors such as strain gauges or load cells that are in electronic communication with a controller controlling the plurality of pressure actuated valves 230. Alternately, the force sensors and pressure transducers may be directly connected with the plurality of pressure actuated valves 230, wherein the plurality of pressure actuated valves 230 may be calibrated in correlation with force or pressure applied on the top layer 210 of the mattress 200. For high density or volume of fluids or for greater speed of operation, additional pumping may be required. Also illustrated in FIG. 1D is control module 1510 which has been included in order to achieve control and automation of several functionalities and features of the bed

1000. The configuration and operation of the control module 1510 has been discussed in detail, later in this description.

In several other embodiments, the bed 1000 may also include a pump unit 150 as illustrated in FIG. 1E. The pump unit 150 is configured to facilitate the transfer of the quantity of the fluid from the mattress 200 to the reservoir 130 and the return of the quantity of the fluid from the reservoir 130 to the mattress 200. The pump unit 150 may again be either located within the frame structure 100 or may be provided inside or attached with an external surface of the mattress 200. In that regard, the pump unit 150 may include a centrifugal pump with a diffuser or a positive displacement type pump such as those comprising a cylinder-piston arrangement or a gear pump. However, mechanisms using gravity feeding and siphoning phenomenon may also be used to at least partially aid the pump assisted fluid flow.

Further, in several embodiments, the mattress 200 may also be provided with predetermined fluid flow channels 250 (250*a*, 250*b*, 250*c*, and 250*d*) in order to allow the fluid pressurized by the pump unit 150, to circulate within the mattress 200 in a predetermined pattern. The predetermined fluid flow channels 250 and consequently the predetermined pattern of fluid flow may be designed in order to provide a massaging effect to the body of the user lying on the mattress. The predetermined fluid flow channels 250 in that regard may be made using a plurality of baffles 240 (240*a*, 240*b*, 240*c*, and 240*d*) that may be adjustable using an adjusting mechanism, for example, including an electrical motor. In that regard, with the adjustment of the plurality of baffles 240, the predetermined fluid flow channels may be modified to provide the massaging effect at several different locations such as pressure points or pulse points or locations relevant to acupressure and acupuncture, etc. In additional embodiments, the mattress 200 may be provided with a foam layer made from a Shape Memory Polymer (SMP). SMP foams have been widely used in the medical services industry to reduce adverse side effects due to long periods of immobility in sickness. Typical foam densities for comfort layers in mattresses vary between 3-6 lb./ft$^3$.

Figure 1F:
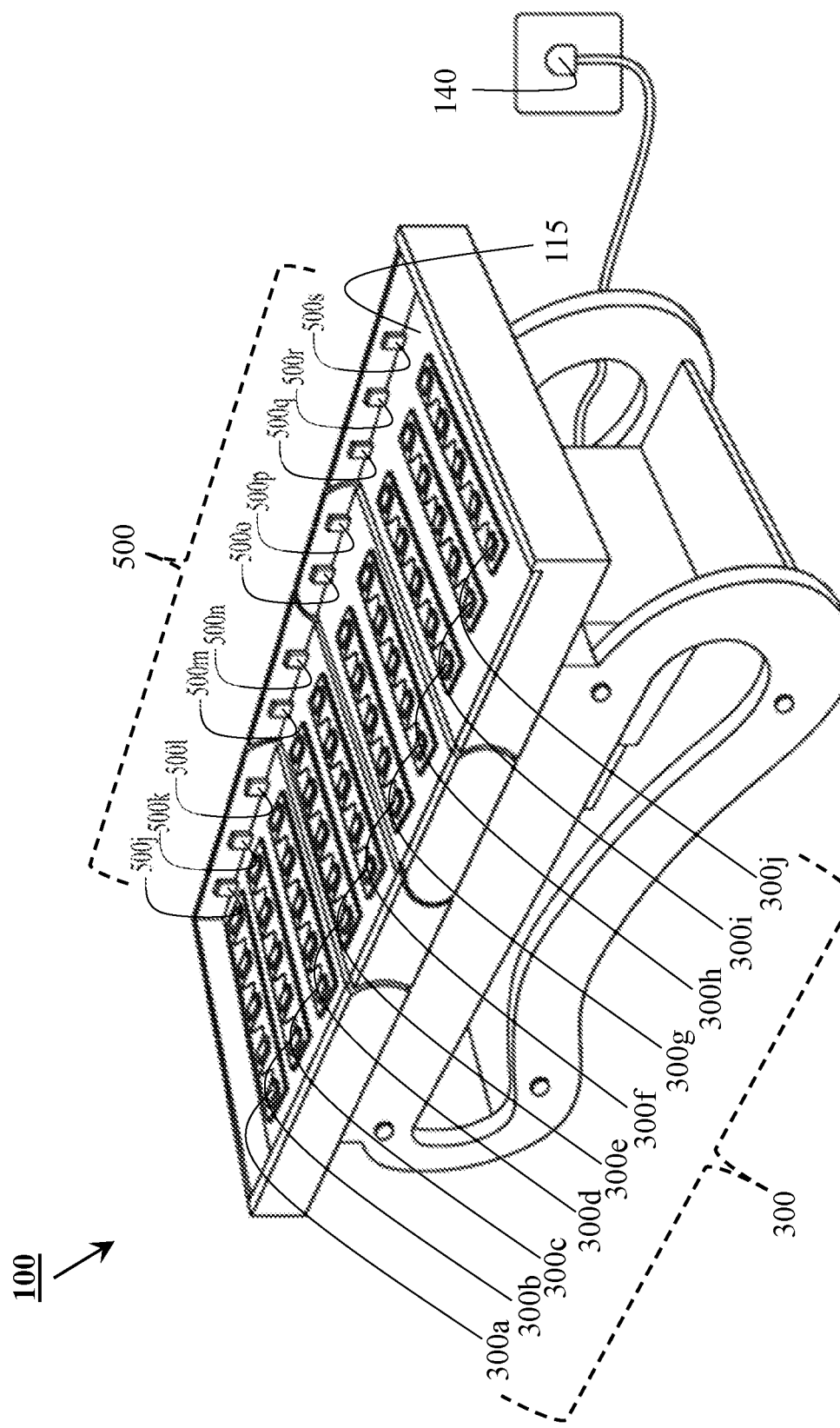
FIG. 1F illustrates a perspective view of the frame structure of the bed illustrated in FIG. 1A.

FIG. 1F illustrates the frame structure 100, in accordance with another embodiment of the present invention. As illustrated in FIG. 1F, the bed 1000 further includes a plurality of Light Emitting Diodes (LEDs) 300 (denoted by LED light strips 300*a*-300*j* with each strip having one or more LEDs) that are configured to emit electromagnetic radiations. Moreover, it is envisaged that during maintenance or reconfiguration for different applications, the LED light strips 300*a*-300*j* may be removable or replaceable. In that regard, the plurality of LEDs 300 may be configured to emit radiation in several frequency bands including infrared, red, blue, green, yellow and other colors in the visible light frequency band. Physiological benefits of LED irradiation can be further studied from Opel D R, Hagstrom E, Pace A K, Sisto K, Hirano Ali S A, Desai S, Swan J. *Light-emitting Diodes: A Brief Review and Clinical Experience. J Clin Aesthet Dermatol.* 2015 June; 8(6):36-44. PMID: 26155326; PMCID: PMC4479368, which is included herein in its entirety, by reference. Some of the key observations derived from the aforementioned art include:

1. Red LEDs specifically have been shown to activate fibroblast growth factor, increase type 1 pro-collagen, increase matrix metallo-proteinase-9 (MMP-9), and decrease MMP-1, thereby acting as an anti-ageing agent.
2. Photomodulated yellow light alters ATP production, gene expression, and fibroblast activity. Increased ATP production is thought to be mediated via the absorption of photons by mitochondrial protoporphyrin IX. Interestingly, only photomodulated yellow LED has been shown to produce a tissue response implying that the light's ability to affect cells is dependent on the number and pattern of photon delivery.
3. Blue light appears to exert its effect on acne via its influence on *Propionibacterium acnes* and its anti-inflammatory properties. *P. acnes* contains naturally occurring porphyrins, mainly coproporphyrin and protoporphyrin IX. Absorption of blue light by these molecules is believed to induce a natural photodynamic therapy (PDT) effect with destruction of the bacteria via the formation of oxygen free radicals. Blue light's anti-inflammatory effect appears to be the result of a shift in cytokine production.
4. Near infrared light, also known as monochromatic infrared energy (MIRE), is believed to stimulate circulation by inducing the release of guanylate cyclase and nitrous oxide, which, in turn, promotes vasodilation and growth factor production as well as angiogenesis, leading to subsequent wound healing.

Furthermore, there is plenty of traditional knowledge in the form of ancient medicines that documents the physiological benefits of light irradiation. For example, the practice of Yoga in India relates mental and physical states of the body with a number of locations within the human body, such locations being termed as "Chakras". As per the literature available, the root chakra (Muladhara chakra) may be activated with red color light, the sacral chakra (Swadhishtana chakra) may be activated with orange color light, the solar plexus chakra (Manipura chakra) may be activated with yellow color light, the heart chakra (Anahata chakra) may be activated with the green color light, the throat chakra (Vishuddha chakra) may be activated with blue color light, the third eye chakra (Ajna chakra) may be activated with indigo color light and the crown chakra (Sahasrara chakra) may be activated with violet color light. Therefore, while in several embodiments, the plurality of LEDs 300 are configured to emit electromagnetic radiations in one or more of red light frequency range and infrared frequency range of the electromagnetic spectrum. Alternately, however, the plurality of LEDs 300 may also be configured to emit electromagnetic radiations in one or more of the visible light frequency range of the electromagnetic spectrum for achieving radiations with different colors.

In construction, the frame structure 100 may include an upper panel 105 (illustrated in FIGS. 1B, 1C and 1D) that is again envisaged to be at least partially transparent. The upper panel 105 may be a surface of a slab made up of glass or a strong and durable polymer material. The mattress 200 as described above may then be placed on the upper panel 105. Further, the plurality of LEDs 300 may be provided on a second surface 115 located at a predetermined depth from the upper panel 105. The upper panel 105, in that regard, in addition to supporting the mattress 200, may also perform the function of protecting the plurality of LEDs 300 against environmental contaminants such as dust, pollen and other kinds of debris. However, the plurality of LEDs 300 may also alternately be located within the mattress 200. For that purpose, it is envisaged that the plurality of LEDs 300 be provided with sufficient sealing in order to prevent it from ingress of the fluid available in the mattress 200. While it is common for the LEDs to include additional optics in form of lenses and reflectors to limit the spread and enhance the intensity of LED irradiation, a resultant beam angle may vary depending upon a specific application. In several embodiments of the invention, each one of the plurality of LEDs 300 further includes a focusing lens configured to confine the emitted electromagnetic radiation within a beam angle within 30 degrees to 60 degrees. The aforementioned range, for the beam angle of 30 degrees to 60 degrees, is envisaged to be most beneficial for therapeutic purposes.

In any of the constructional locations of the plurality of LEDs 300 discussed above, it is further envisaged that in several embodiments of the invention, the plurality of LEDs 300 be mounted on a mounting surface using Surface Mount Technology (SMT). SMT, in contrast to conventional through-hole technology, is a method in which electronic components are mounted or placed directly onto a surface of a Printed Circuit Board (PCB). In that regard, the PCB is provided with flat pads in contrast to holes. The flat pads are called solder pads and can be made from several conducting material compositions such as those including tin-lead, silver or gold plated copper.

Automated Optical Inspection (AOI) systems are commonly used during inspection of the PCBs. SMT technology has proven to be highly efficient for productivity and quality improvements. Other significant benefits include lower costs, increased reliability, and speed of assembling circuit boards while packaging a larger number of components in relatively smaller PCBs. However, the invention is not limited to use of the SMT manufacturing alone, especially in cases where the plurality of LEDs 300 may be frequently connected or disconnected from the frame structure 100 during reconfiguration or maintenance, etc.

Materials used in the plurality of LEDs 300 may vary from one embodiment to another depending upon the frequency of radiation required. Different frequencies can be obtained from LEDs made from pure or doped semiconductor materials. Commonly used semiconductor materials include nitrides of Silicon, Gallium, Aluminum, and Boron, and Zinc Selenide, etc. in pure form or doped with elements such as Aluminum and Indium, etc. For example, red and amber colors are produced from Aluminum Indium Gallium Phosphide (AlGaInP) based compositions, while blue, green and cyan use Indium Gallium Nitride based compositions. White light may be produced by mixing red, green and blue lights in equal proportions, while varying proportions may be used for generating a wider color gamut. White and other colored lightings may also be produced using phosphor coatings such as Yttrium Aluminum Garnet (YAG) in combination with a blue LED to generate white light and Magnesium doped potassium fluorosilicate in combination with blue LED to generate red light. Additionally, near Ultra Violet (UV) LEDs may be combined with europium based phosphors to generate red and blue lights and copper and zinc doped zinc sulfide based phosphor to generate green light.

In addition to conventional mineral based LEDs, the plurality of LEDs 300 may also be provided on an Organic LED (OLED) based flexible panel or an inorganic LED based flexible panel. Such OLED panels may be generated by depositing organic semiconducting materials over Thin Film Transistor (TFT) based substrates. Further, discussion on generation of OLED panels can be found in Bardsley, J. N. (2004), *"International OLED Technology Roadmap"*, *IEEE Journal of Selected Topics in Quantum Electronics*, Vol. 10, No. 1, that is included herein in its entirety, by reference. An exemplary description of flexible inorganic light emitting diode strips can be found in granted U.S. Pat. No. 7,476,557B2, titled "Roll-to-roll fabricated light sheet and encapsulated semiconductor circuit devices", which is included herein in its entirety, by reference.

FIG. 1F also illustrates an electrical power source 140 for the bed 1000. Although shown to be an Alternating Current (AC) power source, the electrical power source may also be a Direct Current (DC) based power source with rectifiers configured to convert the AC power into the DC power. Alternately, the electrical power may also be provided by onboard rechargeable or replaceable batteries. The rechargeable batteries may be based on Nickel Metal Hydride or Lithium-Ion or Lithium-polymer based technologies, or any other technology introduced in foreseeable future.

In continuation of the discussion on installation and operation of the plurality of LEDs 300, the LEDs, in general, are known to generate residual heat at p-n junctions of the LEDs and also where phosphor coatings are used, the temperature of the phosphor particles also shoots up. Especially, in cases of illumination kind LEDs, where radiant energy typically varies between 5 and 40%, the rest of the electrical power supplied to the LEDs is converted into heat energy at their respective p-n junctions. Additionally, the phosphor particles also heat up owing to their limited efficiency in converted absorbed irradiation into emitted irradiation. However, it is important to regulate junction temperatures of the LEDs and phosphor particle temperatures, in order to maintain irradiation intensity and efficiency of the LEDs, ensure sufficient longevity and prevent damage to phosphor material. In that regard, a plurality of temperature sensors 500 (500*j*-500*s*) have also been provided on the frame structure 100 in order to determine temperatures in areas surrounding the plurality of LEDs 300. Additional discussion on locations of the plurality of temperature sensors 500 and the application of corresponding sensor data has been presented in the following discussion.

Figure 2:
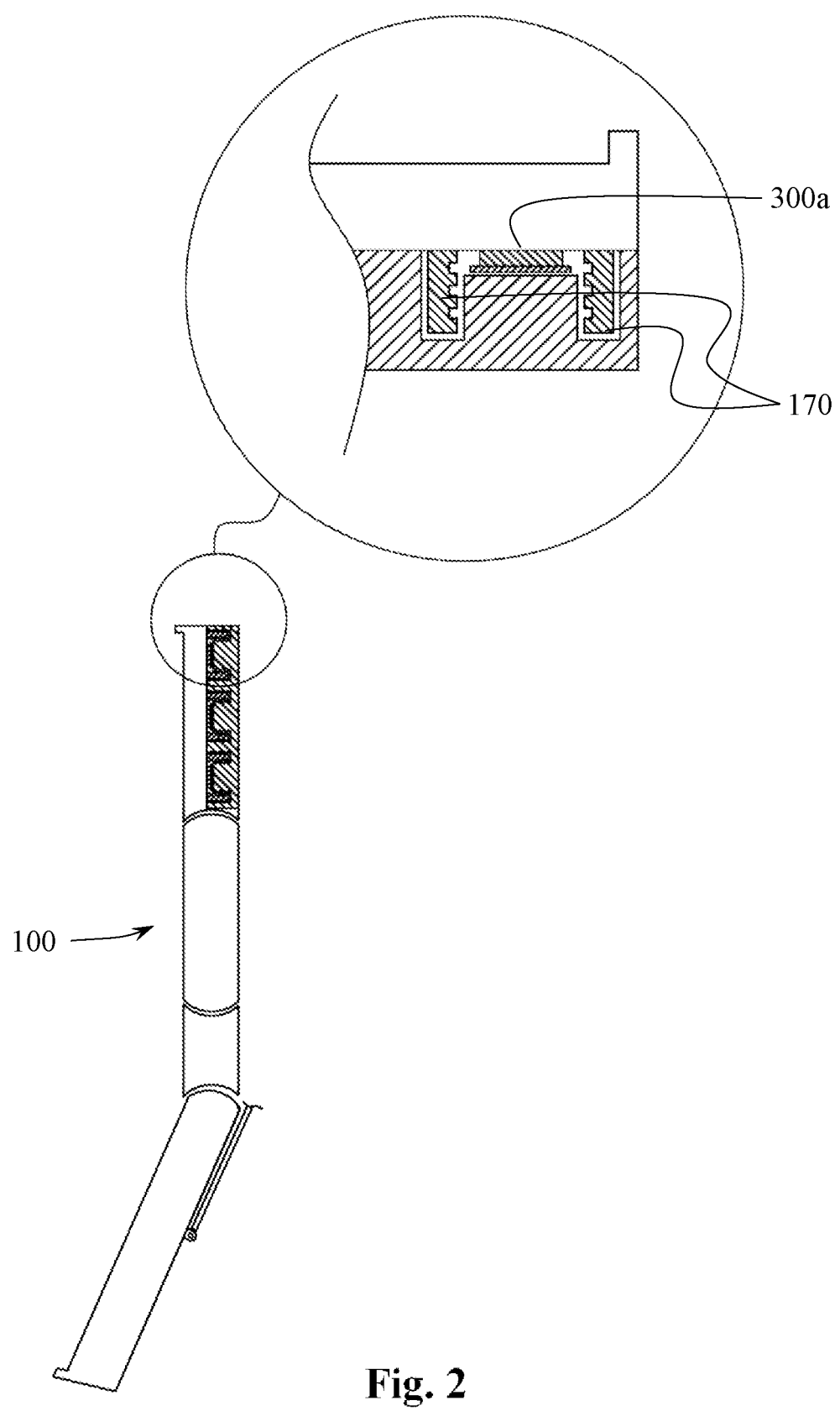
FIG. 2 illustrates a partial sectional view of the frame structure of the bed illustrated in FIG. 1A.

FIG. 2 illustrates a partial sectional view of the frame structure 100 of the bed 1000 illustrated in FIG. 1A. The frame structure 100 has been provided with a heat sink 170 configured to receive heat energy generated by the plurality of LEDs 300. The heat sink 170 provides a channel for the heat energy to be dissipated through any one or more of conduction, convection, and radiation. In general, heat sinks are made from metal and alloys, such as copper and aluminum, having high thermal conductivities. Although, the use of aluminum is more prevalent due to high costs and lower fusion temperatures of copper and its alloys. In certain, lower heat dissipation applications, the heat sinks may also be constructed from thermoplastic materials. Moreover, in certain specific applications, graphite may also be used as a material for the construction of the heat sink.

The heat sink 170 may be provided as, but not limited to, a pad, a tape, a strip, a plate or a mounting body for the plurality of LEDs 300. Some of the commonly known heat sink constructions include, but are not limited to, anodized extruded linear heat sinks, LED housings, LED light engine housings, aluminum stocks, and small finned heat sinks. However, the selection of a particular construction for the heat sink will depend upon several factors such as LED wattage, number of LEDs, ambient conditions, and whether the LEDs are being mounted in a relatively open space or a relatively enclosed cavity. Several fins extending into the ambient may also be provided to increase the overall surface area of the heat sink for greater heat dissipation.

Additionally, the heat sink may 170 be mounted using a thermally conducting adhesive and may be enriched with additional post-processing operations such as painting, anodizing and etching to decrease their thermal resistance and increase heat dissipation efficiencies. Moreover, in several embodiments, to enhance the heat dissipation from the heat sink 170, additional ventilation in form of forced or induced draft of air, may be provided by using a fan assembly provided in the frame structure 100. Again, the selection of the fan assembly will depend upon factors such as maintenance, cost, reliability, noise, and packaging issues.

Figure 3:
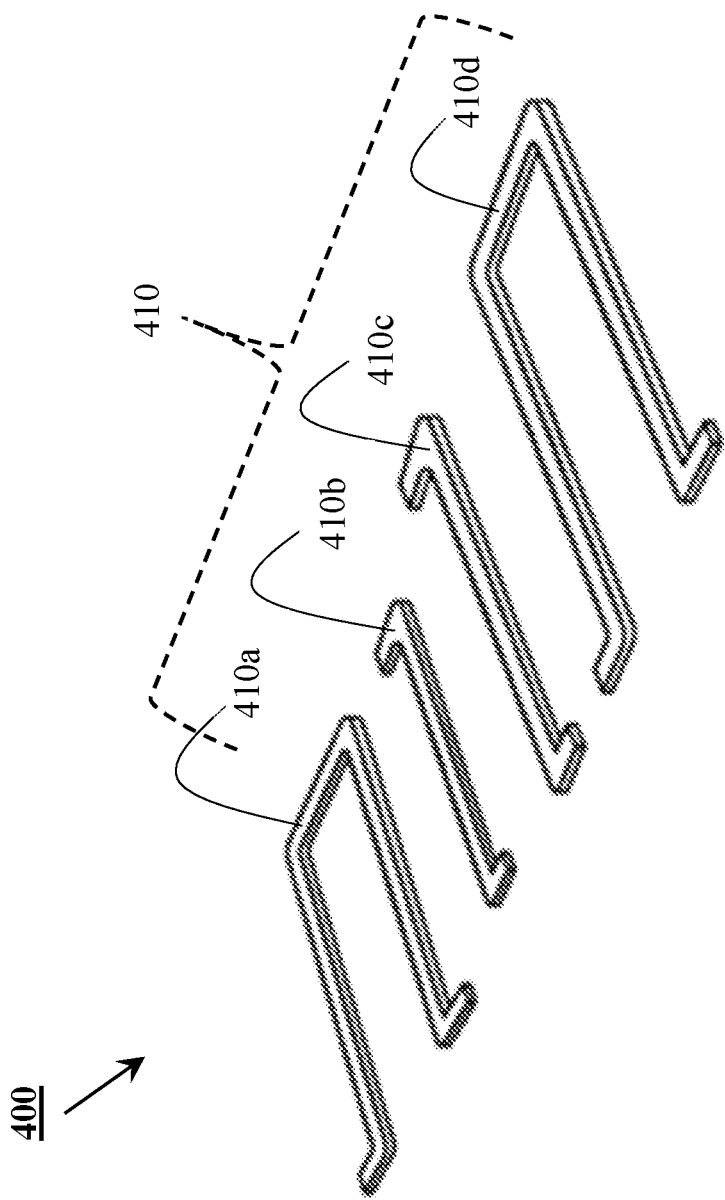
FIG. 3 illustrates a plurality of flexible heating elements of an infrared heater of the bed illustrated in FIG. 1A.

FIG. 3 illustrates a plurality of flexible heating elements 410 (410*a*, 410*b*, 410*c* and 410*d*) of the infrared heater 400 of the bed 1000 illustrated in FIG. 1A. It is envisaged here, that in several embodiments, although not bindingly, the infrared heater 400 be a far infrared type of heater. Typically, infrared heaters operate by providing long, medium and short-wave infrared radiations having wavelengths between 15 micrometers to 1 millimeter. Human skin absorbs far infrared radiations specifically well due to the skin composition comprising at least seventy percent of water. Additionally, the infrared heaters have the advantage of not giving off smell from dust, dirt, formaldehyde and toxic fumes from paint coating, etc. Therefore, they are suitable for human use as they are less likely to cause skin irritations and sensitivities.

The plurality of flexible heating elements 410 may be manufactured in the form of cords bundling several individual flexible strings. Such flexible strings may be made from carbon, or ceramic material or a combination of ceramic material and carbon. The ceramic materials used in such applications typically utilize Mixed Metal Oxides (HMOs) that are compounds including oxides of two or more metals. Some of the exemplary metals used in HMOs include copper, cobalt, iron, trivalent chrome, tin, antimony, titanium, manganese, and aluminum, etc. The use of the ceramic materials at least in part ensures achieving higher emissivity as compared to using pure carbon alone as heating material. It is also to be noted that heating of the plurality of flexible heating elements 410 is achieved through applying a potential difference along the plurality of flexible heating elements 410. The electrical resistance of the plurality of flexible heating elements 410 causes heat to be dissipated from the plurality of flexible heating elements 410.

FIGS. 3 and 1A illustrate an exemplary arrangement of the plurality of flexible heating elements 410 of the infrared heater 400, in accordance with an embodiment of the present invention. It can be observed through FIGS. 1A and 3, that the plurality of flexible heating elements 410 are arranged in such a manner that they coil around the plurality of LEDs 300 along the second surface 115 of the frame structure 100. In several alternative embodiments, however, the plurality of flexible heating elements 410 are located within the mattress 200 and may draw electrical power from plugging onto the frame structure 100 or may carry a dedicated power source for the infrared heater 400 in form of rechargeable or replaceable battery.

Figure 4A:
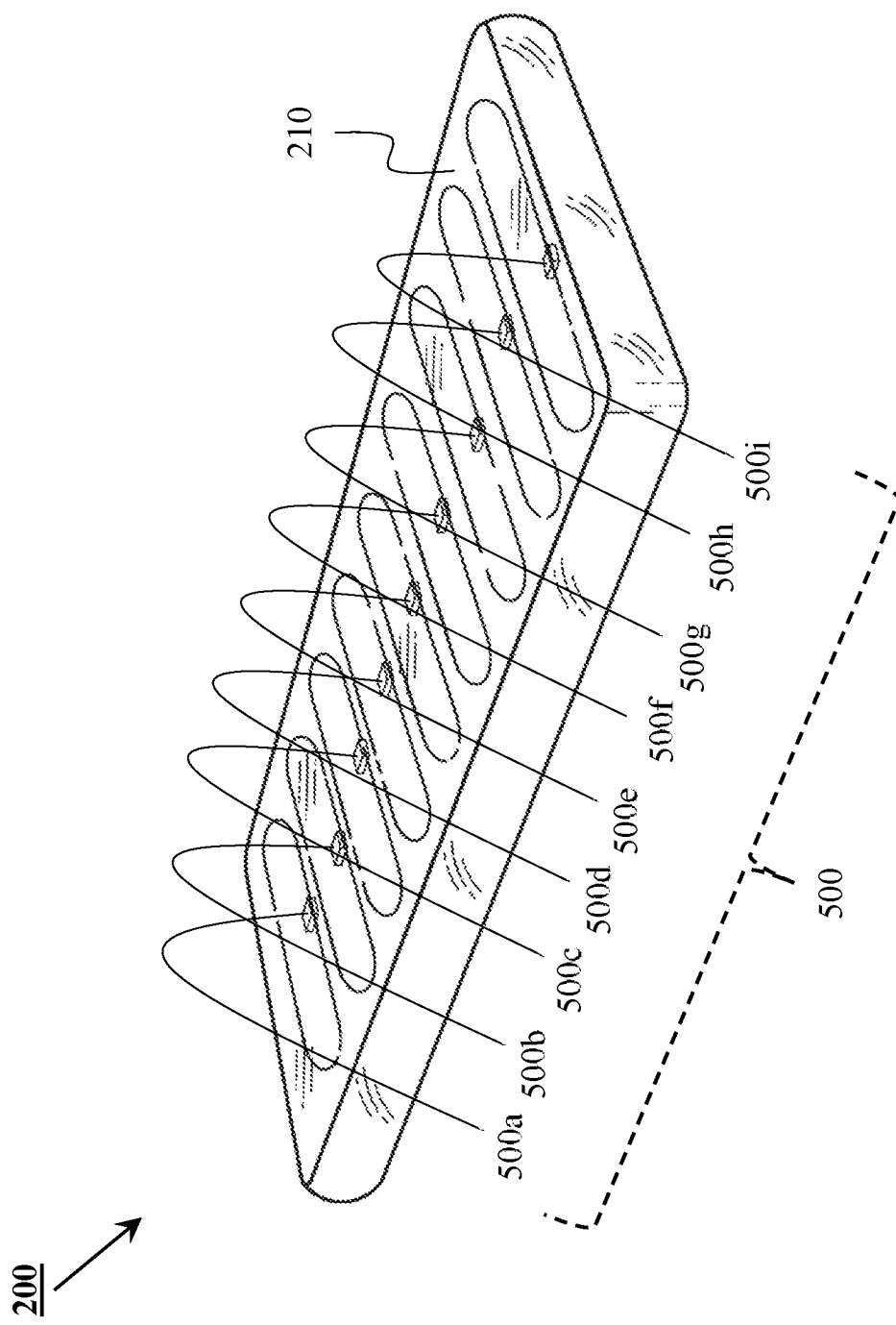
FIG. 4A illustrates the mattress for the bed illustrated in FIG. 1A.

FIG. 4A illustrates the mattress 200 for the bed 1000 illustrated in FIG. 1A. Referring to FIGS. 1F and 5A, the bed 1000 has been provided with the plurality of temperature sensors 500 (500*a* to 500*s*) provided at a plurality of locations on the frame structure 100 and the mattress 200 in order to generate signals in correlation with temperature values at the plurality of locations. In that regard, the plurality of temperature sensors 500 can be any one or more of, but not limited to, thermocouple or semiconductor-based temperature sensors. The signals may then be transmitted to the control module 1510 including a processor (illustrated later as 1512) that may control the operation of one or more of the plurality of LEDs 300, the infrared heater 400 and the pump unit 150 to maintain the temperature values within respective predetermined ranges. More discussion on control architecture of the bed 1000 including the frame structure 100 and the mattress 200 has been provided later in the discussion.

In several embodiments of the invention, the bed 1000 also includes a plurality of auxiliary sensors configured to obtain a plurality of auxiliary measurements of the body of the user. In that regard, the plurality of auxiliary sensors may include but are not limited to, heart rate sensors and sweat rate sensors. In that regard, the heartbeat of the user may be determined using heart rate sensors deploying electrical means (generating an electrical signal on radio-detection of a heartbeat) or optical means (measuring scattering of visible light due to change of blood flow in blood vessels). Perspiration measurement for the body of the user can be obtained through the sweat rate sensors that typically include a humidity chamber for collecting sweat and humidity sensors (for example, capacitive thin filmed humidity sensors), for determining the sweat rate.

Figure 4B:
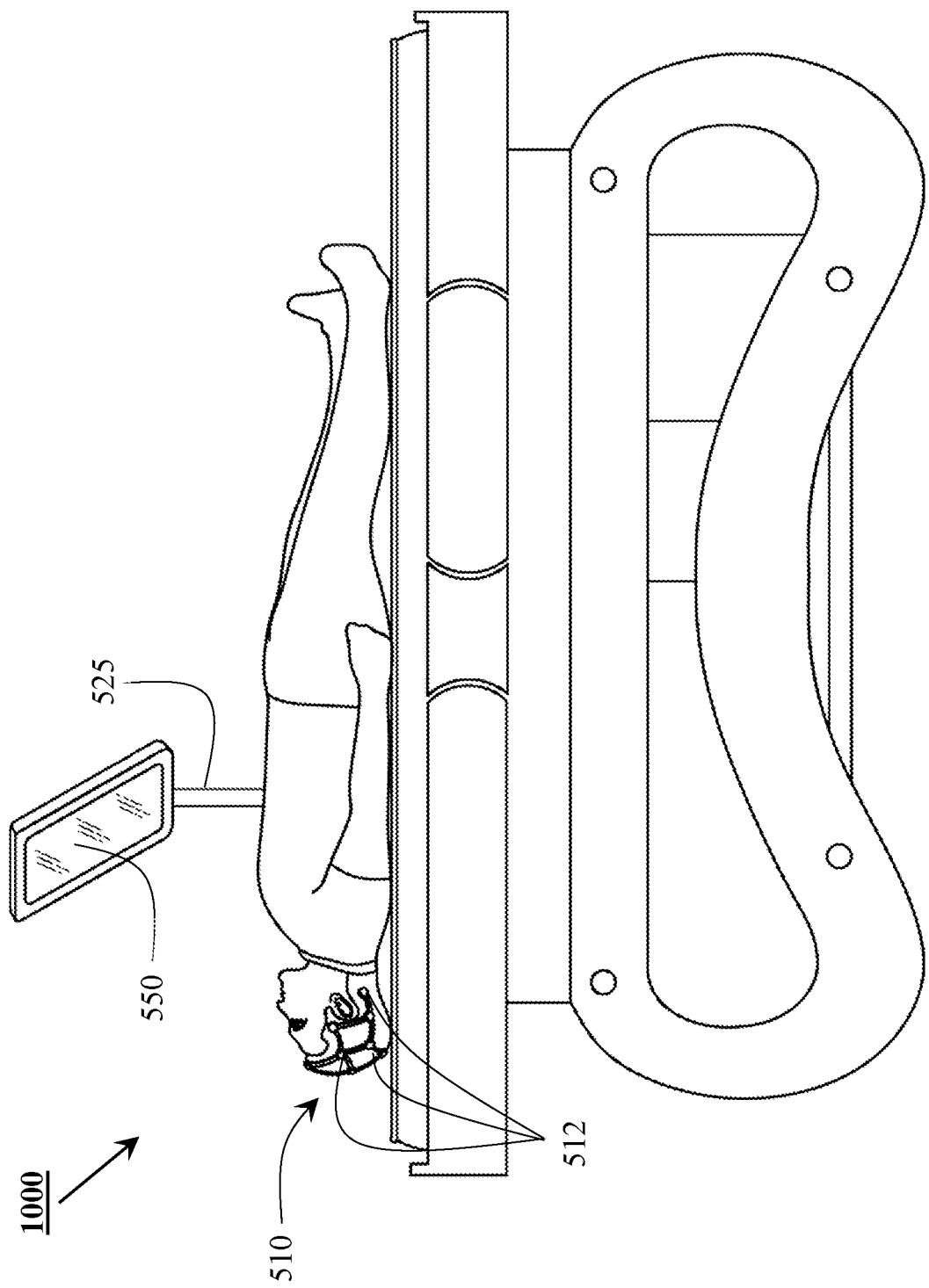
FIG. 4B illustrates the bed illustrated in FIG. 1A with an additional fastening arrangement capable of holding a computing device.

FIG. 4B illustrates the bed 1000 illustrated in FIG. 1A, with an additional fastening arrangement 525 capable of holding a computing device 550. The fastening arrangement 525 in that regard may include an extendible frame for the computing device 550 that may include stretchable materials, springs, and a backing plate, etc. As also illustrated in FIG. 4B, the plurality of auxiliary sensors also include an Electro-Encephalogram (EEG) unit 510. The EEG unit 510 includes a plurality of metal electrodes 512 that may be attached to the scalp of the user for determining electrical activity within the brain of the user. The EEG unit 510 may be instrumental in determining and treating the mental conditions of the user, such as sleep disorders and mood swings to provide a calming effect on the user.

It is further envisaged that the bed 1000 be capable of being controlled remotely, and be configured as per specifications desired by the user. Further, the bed 1000 in itself should be able to carry out some preconfigured functions depending upon a specific application. In that manner, the bed 1000 has been provided with a control architecture which will be discussed below. The control architecture has been elucidated only in a logical capacity, the actual construction and configurations may vary from one application to another, based on factors such as but not limited to, variations in height, weight and Body Mass Index (BMI) of the user, routine activities and sleeping patterns of the user, geographical locations and their corresponding climactic factors, where the bed 1000 is being used, kind of applications such as therapeutic (skin and muscle pain) or recreational (skin tanning or body massaging), etc., and specific hardware/software/firmware functionalities as desired in a particular market.

Figure 5:
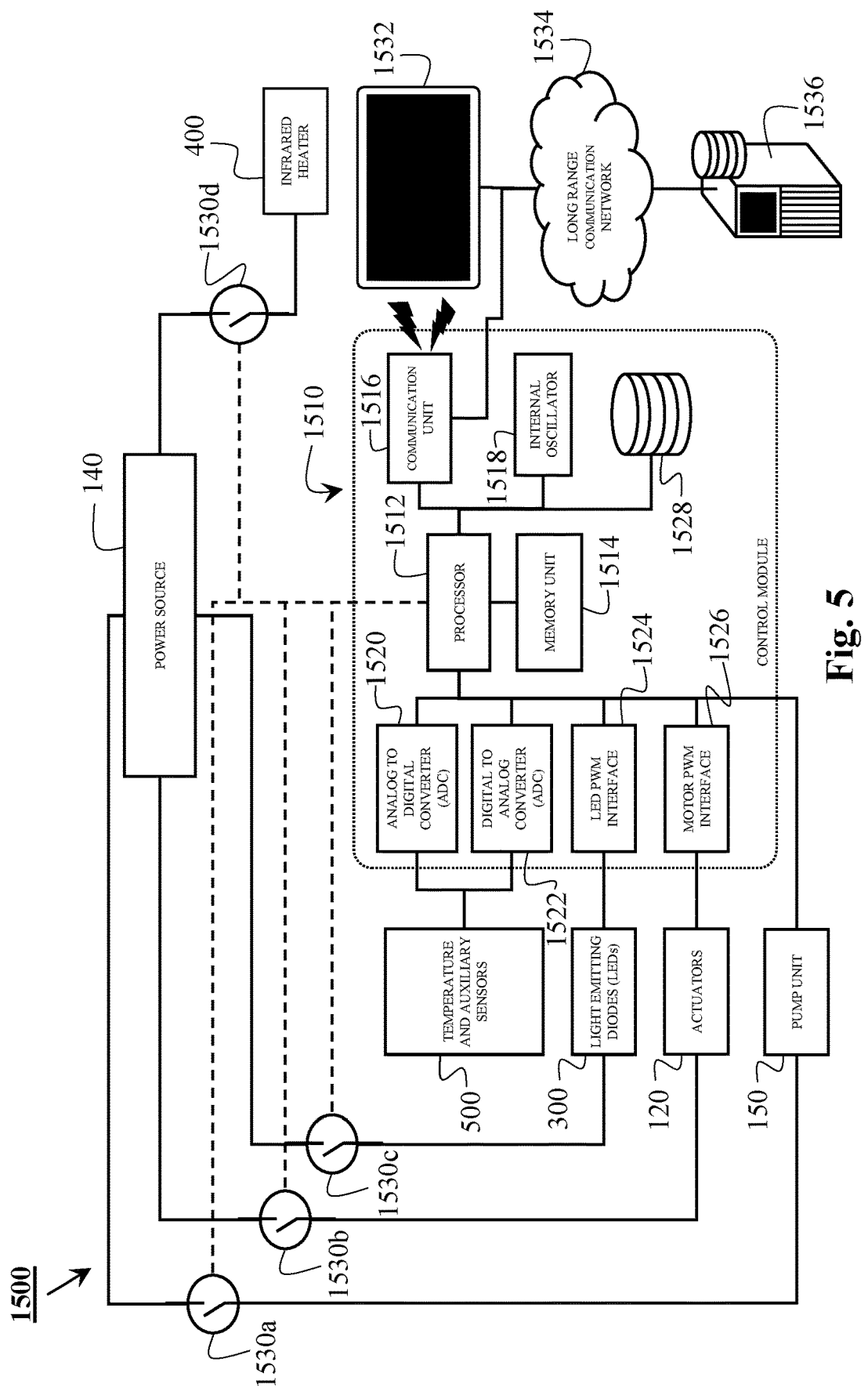
FIG. 5 illustrates a logical diagram of a control architecture provided with the bed, in accordance with an embodiment of the present invention.

FIG. 5 illustrates a logical diagram of a control architecture 1500 provided with the bed 1000, in accordance with an embodiment of the present invention. The control architecture 1500 as depicted includes the control module 1510 including a processor 1512, a memory unit 1514, a communication unit 1516, a non-volatile storage device 1528, an internal oscillator clock 1518 for time keeping, an Analog to Digital Converter (ADC) 1520, a Digital to Analog Converter (DAC) 1522, an LED Pulse Width Modulation (PWM) interface 1524 for control of emission characteristics of the plurality of LEDs 300 and a motor PWM interface 1526 for control of the one or more actuators 120 in case the one or more actuators 120 include electrical motors. FIG. 5 also illustrates a plurality of control switches 1530 (1530*a*, 1530*b*, 1530*c* and 1530*d*) for control and automation of field devices such as the plurality of LEDs 300, the one or more actuators 120, the pump unit 150 and the infrared heater 400.

In that regard, the plurality of control switches 1530 may be of electromechanical in construction (such as relays) or may be solid state switches (such as transistors) and may be activated or deactivated to prevent the supply of the electrical power to the field devices, from the electrical power source 140. The stippled (or dashed) lines shown connecting the processor 1512 with the plurality of control switches 1530 are indicative of communication mediums and protocols, such as Controller Area Network (CAN) bus or Process Field Bus (PROFIBUS), used for automation and control of the field devices as listed above.

The processor 1512 may be a general-purpose processor, a Field Programmable Gate Array (FPGA) or an Application Specific Integrated Circuit (ASIC), etc. Additionally, the memory unit 1514 may be a volatile memory unit such as Static Random Access Memory (SRAM) and Dynamic Random Access Memory (DRAM) of types such as Asynchronous DRAM, Synchronous DRAM, Double Data Rate SDRAM, Rambus DRAM, and Cache DRAM, etc. The non-volatile storage device 1528 may be EPROM, EEPROM or flash memory based storage device. The communication unit 1516 allows the bed 1000 and more specifically the control module 1510 to communicate with external devices such as a computing device 1532. In that regard, the computing device 1532 may be a smartphone, a Personal Digital Assistant (PDA), a tablet PC, a wired or wireless remote controller or the like.

In that regard, the communication may be carried out through wired media such as those implementing IEEE 802.3 Ethernet standard or wireless media such as those implementing Bluetooth, ZigBee, Near Field Communication (NFC) and 802.11 Wireless Fidelity (Wi-Fi) or combinations thereof. In that regard, the communication unit 1516 may include a port such as an Ethernet port or a Universal Serial Bus (USB) port or may be provided with a radio frequency transceiver. The communication unit 1516 may also be able to communicate with a media database server 1536 through a long range communication network 1534, such as Internet implemented through one or more protocols such as LTE, HSDPA, HSPA, GSM, 802.3 (Ethernet) and 802.11 (Wi-Fi), etc., standardized by Standard Setting Organizations such as 3GPP, IEEE or the like.

Figure 6:
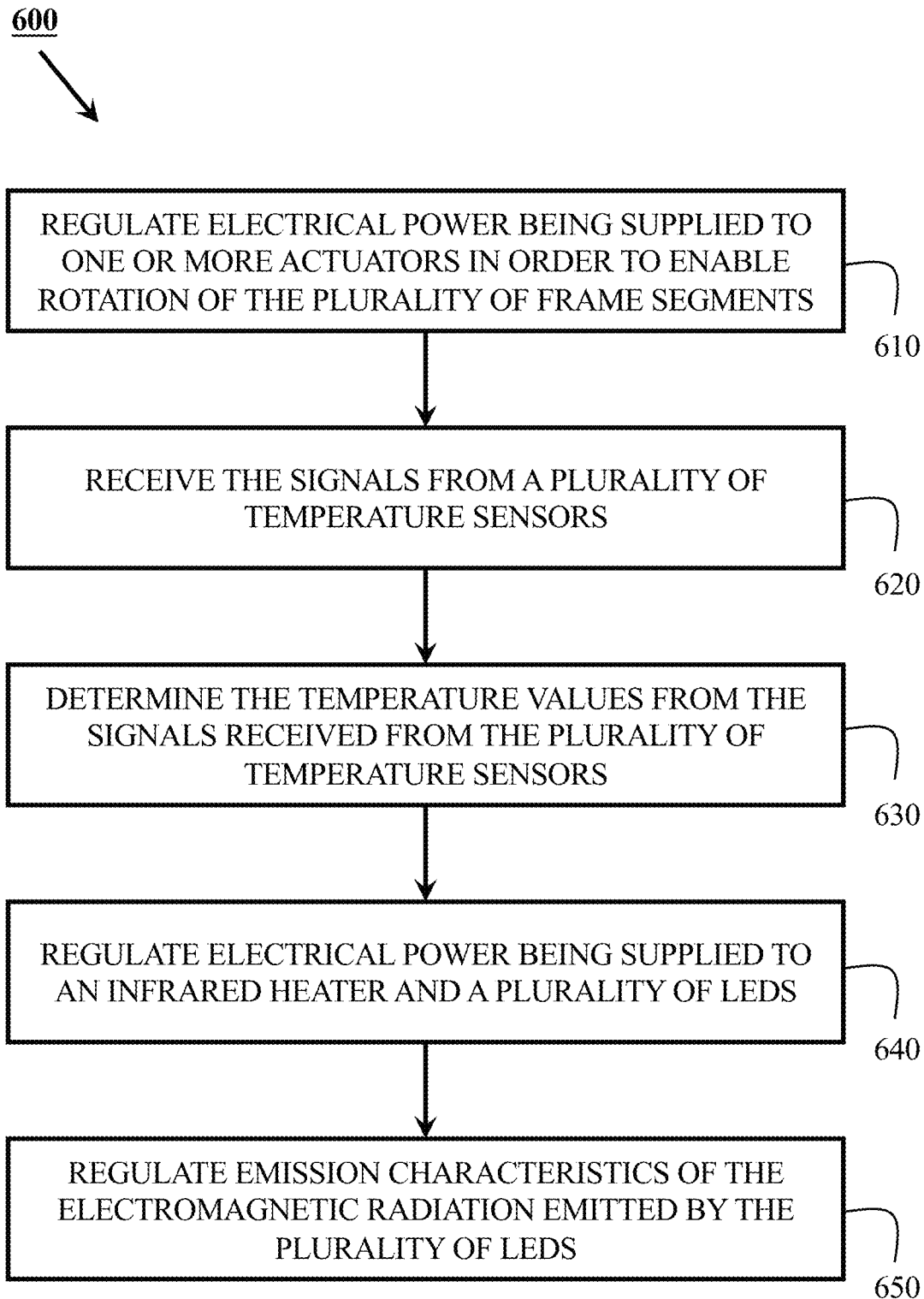
FIG. 6 illustrates a method for utilizing the bed for therapeutic and recreational applications, in accordance with an embodiment of the present invention.

FIG. 6 illustrates a method 600 for utilizing the bed 1000 for therapeutic and recreational applications, in accordance with an embodiment of the present invention. The method steps being described below are envisaged to be performed by the processor 1512 executing machine readable instructions stored in the memory unit 1514. The method begins at step 610 when a user lies down on the mattress 200, and based on a control signal received via the communication unit 1516, the processor 1512, regulates electrical power being supplied to the one or more actuators 120 in order to enable rotation of the plurality of frame segments 110, to enable posture adjustment of the user. In that regard, the processor 1512 may activate or deactivate a second control switch 1530b controlling power to the one or more actuators 120 and modulating power to each one of the one or more actuators 120 using the motor PWM interface 1526. In several alternative embodiments, the one or more actuators 120 may be further used to slide the plurality of frame segments 110 linearly, for adjustment of the frame structure 100 to accommodate the height of the user. In that case, if the one or more actuators 120 happen to be electrical rotary motors, sufficient mechanisms may be used to convert the rotary motion of the electrical motors to linear sliding motions of the plurality of frame segments 110.

Alternately, if the one or more actuators 120 happen to be hydraulic or pneumatic actuators, sufficient mechanism may be used to convert linear motions of the one or more actuators 120 into rotary motion wherever needed. In several alternative embodiments, combinations of motors, hydraulic and pneumatic actuators may also constitute the one or more actuators 120. Moreover, the processor 1512 may activate the pump unit 150 in order to allow at least a quantity of the fluid to be transferred to the reservoir 130 so that the top layer 210 can conform to the body shape of the user.

At step 620, the processor 1512 receives the signals transmitted by the plurality of temperature sensors 500. Further, at step 630, the processor 1512 determines the temperature values from the signals received from the plurality of temperature sensors 500. The temperature values may indicate the temperatures at several locations within the frame structure 100 and the mattress 200, such as at the surfaces in direct contact with the body of the user, the junction temperatures of the plurality of LEDs 300, the phosphor particle temperatures and the like. In that regard, to maintain the temperature values within predetermined ranges, the processor 1512, at step 640, regulates electrical power being supplied to the infrared heater 400 and the plurality of LEDs 300 in correlation with the determined temperature values. At step 650, depending upon several parameters such as, but not limited to, variations in height, weight and Body Mass Index (BMI) of the user, routine activities and sleeping patterns of the user, geographical locations and their corresponding climactic factors, and kind of application of the bed 1000, the processor 1512 regulates emission characteristics of the electromagnetic radiation emitted by the plurality of LEDs 300. For example, depending upon a specific application, the electromagnetic radiation may be in red or infrared frequency range or in any other frequency range lying within the visible light band of the electromagnetic spectrum.

Alternately, in several embodiments, the user may also be able to control emission characteristics of the plurality of LEDs 300, and the heat energy provided by the infrared heater 400, using the computing device 1532. In that regard, the processor 1512 may receive a control input from the computing device 1532, being operated by the user. Further, the processor 1512, may modify the one or more of the emission characteristics of the electromagnetic radiation and heat generated by the infrared heater 400, in correlation with the received control input. In addition, in correlation with the control input received from the user, the processor 1512 may also regulate the electrical power being supplied to the one or more actuators 120 in order to enable rotation of the plurality of frame segments 110 for adjusting body posture, regulate power being supplied to the pump unit 150 for inflow and outflow of the fluid from the mattress 200, in order to enable shape conformity of the mattress 200 with the body of the user, reorient the plurality of baffles 240 provided within the mattress 200, to direct massaging effect to a predetermined part of the body or operate the EEG unit 510.

The processor 1512 may also be able to execute a media file in response to receiving the control input and may execute the media file in correlation with the control input, by fetching the media file from the media database server 1536, using an Application Program Interface (API), via the long range communication network 1534. However, in several other embodiments, the processor 1512 executes the media file in correlation signals provided by the plurality of auxiliary sensors. For example, if the heart rate sensor is providing a signal correlating with an increased heart rate of the user, the processor 1512 will execute a classical music file in order to lower the heart rate of the user. Similarly, parameters like tempo, volume, rhythm, and genre, etc. may also be selected in accordance with the signals provided by EEG unit 510 of the bed, in order to balance the mental state of the user or regulate sleep patterns.

Figure 7:
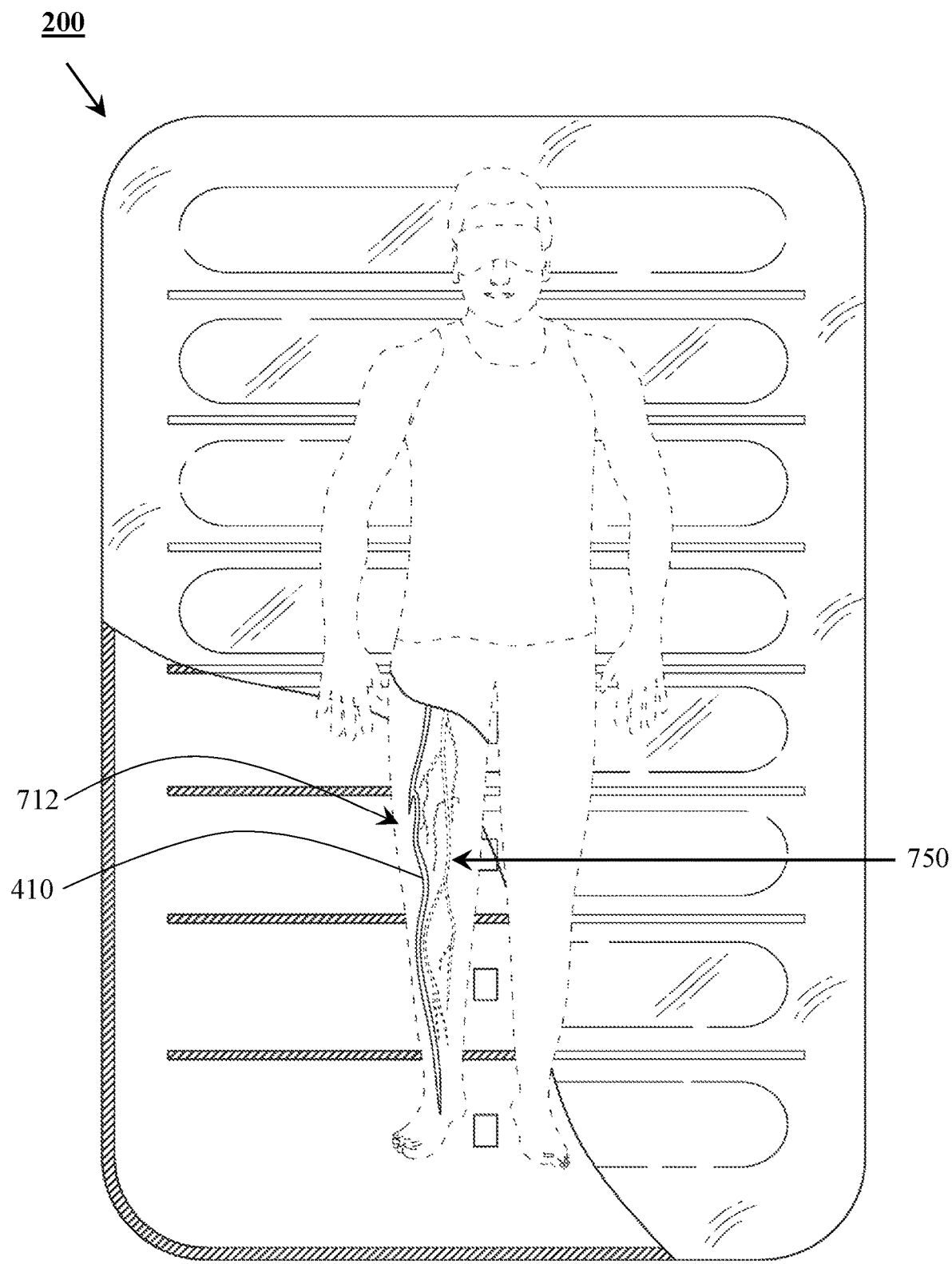
FIG. 7 illustrates the mattress in accordance with another embodiment of the present invention.

The construction of the frame structure 100 and the mattress 200, however, is not limited to what has been discussed in the preceding discussion. For example, the mattress 200 and the frame structure 100 may be embodied in several other forms, without departing from the scope of the invention. FIG. 7 illustrates the mattress 200 in accordance with another embodiment of the present invention. As illustrated in FIG. 7, the plurality of flexible heating elements 410 align with superficial veins 750 of the body of the user. Superficial veins are typically located parallel to the body surface, in the fat layer, between the skin and fascia covering muscle tissues. This is to ensure that while heating, the heat is directly supplied to veins causing the veins to expand and therefore allowing a greater flow of blood and supply of oxygen to several organs inside the body. Also, it is medically known that veins carry colder blood when compared to arteries, hence it would be intuitive to apply heating directly to the veins in order to speed up the blood flow to the heart of the user.

It is envisaged here that small adjustments may be possible in the locations of the plurality of flexible heating elements 410 in order to accommodate for varying body shapes and sizes of several potential users. In that manner, the plurality of flexible heating elements 410 have been located in a plurality of respective grooves 712 in a fabric of the top layer 210 of the mattress 200 and a predetermined amount of clearance may be provided in the plurality of grooves 712, to allow for the adjustment of the plurality of flexible heating elements 410. The elasticity and stretchability of fabric of the top layer 210 would allow the plurality of flexible heating elements 410 to remain in their respective locations, once the plurality of flexible heating elements 410 have been adjusted to their respective positions, by the user. In several embodiments, the plurality of flexible heating elements 410 may be connected with a dedicated power source (such as a battery or a terminal of a power module encapsulating the battery) through detachable connectors. Such detachable connectors would allow for the amount of current being supplied to the plurality of flexible heating elements 410, be controlled and convenient replacement in a situation where anyone of the plurality of flexible heating elements 410 is damaged or dysfunctional. As discussed above, maintenance of regulated temperature values in areas directly in contact with a body of a user, power electronic circuitry and thermally fusible surfaces may be essential for the longevity of the bed 1000.

Figure 8:
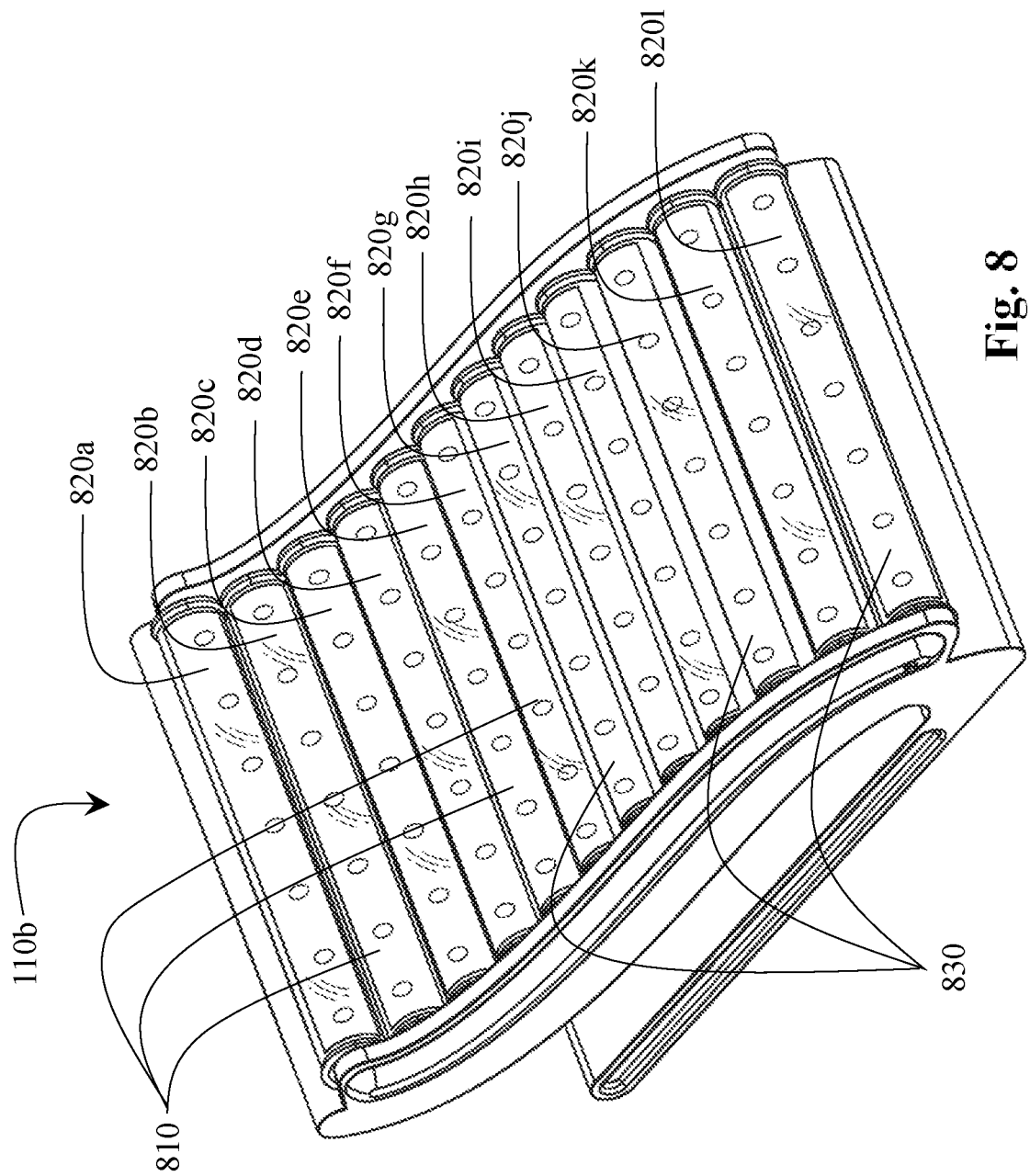
FIG. 8 illustrates the construction of the frame structure, in accordance with another embodiment of the present invention.

FIG. 8 illustrates the construction of the frame structure 100, in accordance with another embodiment of the present invention. As illustrated in FIG. 8, a frame segment 110*b* of the frame structure 100 includes a plurality of discrete longitudinal structures 810. Further, the plurality of longitudinal structures 810 include a plurality of respective slats 820 (820*a* to 820*l*), the plurality of LEDs 300 being divided amongst the plurality of slats 820. Also, the mattress 200 has been divided into a plurality of mattress segments 830 provided within the plurality of respective longitudinal structures 810, the plurality of mattress segments 830 provided on the plurality of respective slats 820.

The bed as described through several embodiments offers a number of advantages. The bed is simpler in construction and easy to operate either through a remote control or a handheld device. Further, the bed combines a number of therapeutic and recreational benefits such as sauna, skin treatment, pain relief, muscle relaxation, and reformation. Additionally, the bed is customizable for a number of varied applications without making any significant constructional changes. The use of LEDs as lighting sources and infrared heater as a heating source ensures minimal power consumption when compared with other solutions available in the art. The bed is therefore very well suited for both recreational use and non-invasive therapies without causing skin sensitivities or any kind of allergic reactions that may be caused due to other pharmaceutical therapies or cosmetic procedures etc.

The programming instructions can be, for example, computer-executable and/or logic implemented instructions. In some examples, a computing device is configured to provide various operations, functions, or actions in response to the programming instructions conveyed to the computing device by one or more of the computer-readable medium, the computer recordable medium, and/or the communications medium. The non-transitory computer-readable medium can also be distributed among multiple data storage elements, which could be remotely located from each other. The computing device that executes some or all of the stored instructions can be a micro-fabrication controller or another computing platform. Alternatively, the computing device that executes some or all of the stored instructions could be remotely located computer systems, such as a server.

Further, while one or more operations have been described as being performed by or otherwise related to certain modules, devices or entities, the operations may be performed by or otherwise related to any module, device or entity. As such, any function or operation that has been described as being performed by a module could alternatively be performed by a different server, by the cloud computing platform, or a combination thereof. Further, the operations need not be performed in the disclosed order, although in some examples, an order may be preferred. Also, not all functions need to be performed to achieve the desired advantages of the disclosed system and method, and therefore not all functions are required.

Various modifications to these embodiments are apparent to those skilled in the art, from the description and the accompanying drawings. The principles associated with the various embodiments described herein may be applied to other embodiments. Therefore, the description is not intended to be limited to the embodiments shown along with the accompanying drawings but is to be providing broadest scope of consistent with the principles and the novel and inventive features disclosed or suggested herein. Accordingly, the invention is anticipated to hold on to all other such alternatives, modifications, and variations that fall within the scope of the present invention and appended claims.

The invention claimed is:

1. A bed for therapeutic and recreational applications, the bed comprising:
   a frame structure,
   a mattress provided on the frame structure of the bed,
   a plurality of Light Emitting Diodes (LEDs) configured to emit electromagnetic radiation,
   an infrared heater assembly provided within the frame structure, the infrared heater assembly including a plurality of flexible heating elements connected with a power source,
   a plurality of temperature sensors provided at a plurality of locations on the frame structure and the mattress in order to generate signals in correlation with temperature values at the plurality of locations,
wherein the frame structure includes a plurality of frame segments adapted to rotate to respective predetermined angles, in order to lift or recline, with respect to a locating surface on which the bed has been located, the rotation of the plurality of frame segments being achieved through one or more actuators, and
wherein the mattress is made from at least partially transparent material and includes a fluid that is at least partially transparent.

2. The bed as claimed in claim 1, wherein the frame structure includes an upper panel, the upper panel being at least partially transparent, the mattress being provided on the upper panel of the frame structure,
wherein the plurality of LEDs have been provided on a second surface at a predetermined depth from the upper panel, and
wherein the plurality of flexible heating elements are provided along the second surface.

3. The bed as claimed in claim 1, further comprising a plurality of auxiliary sensors configured to obtain a plurality of auxiliary measurements.

4. The bed as claimed in claim 3, wherein the plurality of auxiliary sensors include an Electro-Encephalogram (EEG) unit.

5. The bed as claimed in claim 1, further comprising a reservoir, wherein the mattress includes a plurality of pressure-activated valves that allow a quantity of the fluid to be transferred to the reservoir when pressure is applied on a top surface of the mattress and allow the transferred quantity to be returned to the mattress when the pressure is released.

6. The bed as claimed in claim 5, further comprising a pump unit, wherein the pump unit is configured to facilitate the transfer of the quantity of the fluid from the mattress to the reservoir and the return of the quantity of the fluid from the reservoir to the mattress.

7. The bed as claimed in claim 6, wherein the mattress has been provided with predetermined fluid flow channels in order to allow the fluid pressurized by the pump unit, to circulate within the mattress, in a predetermined pattern.

8. The bed as claimed in claim 1, wherein the plurality of LEDs are configured to emit electromagnetic radiations in one or more of red light frequency range and infrared frequency range of the electromagnetic spectrum.

9. The bed as claimed in claim 1, wherein the plurality of LEDs are configured to emit electromagnetic radiations in one or more frequencies of visible light frequency range of the electromagnetic spectrum.

10. The bed as claimed in claim 1, wherein the plurality of LEDs are provided on one or more of flexible Organic LED (OLED) and inorganic LED based panels.

11. The bed as claimed in claim 1, wherein a frame segment of the plurality of frame segments, includes:
a plurality of discrete longitudinal structures,
wherein the plurality of longitudinal structures include a plurality of respective slats, the plurality of LEDs being divided amongst the plurality of slats, and
wherein the mattress has been divided into a plurality of mattress segments provided within the plurality of respective longitudinal structures, the plurality of mattress segments provided on the plurality of respective slats.

12. The bed as claimed in claim 1, wherein the fluid is selected from a group comprising water, a gel, and combinations thereof.

13. The bed as claimed in claim 1, further comprising a processor and a memory unit, the memory unit comprising machine-readable instructions, the machine-readable instructions when executed by the processor, enables the processor to:
receive the signals from the plurality of temperature sensors,
determine the temperature values from the signals received from the plurality of temperature sensors,
regulate electrical power being supplied to the infrared heater and the plurality of LEDs in correlation with the determined temperature values,
regulate emission characteristics of the electromagnetic radiation emitted by the plurality of LEDs, and
regulate electrical power being supplied to the one or more actuators in order to enable rotation of the plurality of frame segments.

14. The bed as claimed in claim 13, wherein the processor is further enabled to execute a media file in correlation with signals provided by a plurality of auxiliary sensors.

15. The bed as claimed in claim 13, further comprising a communication unit capable of communicating with a computing device through one or more of a short range and a long range communication network, wherein the processor is further enabled to:
receive a control input from the computing device, and in correlation with the control input, perform one or more of:
modify the one or more of the emission characteristics of the electromagnetic radiation and heat generated by the infrared heater,
regulate the electrical power being supplied to the one or more actuators in order to enable the rotation of the plurality of frame segments,
regulate power being supplied to a pump unit provided with the bed, in order to enable shape conformity of the mattress with a body of a user,
reorient a plurality of baffles provided within the mattress to direct massaging effect to a predetermined part of the body, and
operate an EEG unit provided within the bed.

16. A frame structure of a bed for therapeutic and recreational applications, the frame structure comprising:
a plurality of Light Emitting Diodes provided within the frame structure and configured to emit electromagnetic radiation,
an infrared heater assembly provided within the frame structure, the infrared heater assembly including a plurality of flexible heating elements connected with a power source,
a plurality of temperature sensors provided at a plurality of locations on the frame structure, and
wherein the frame structure includes a plurality of frame segments adapted to rotate to respective predetermined angles in order to lift or recline the plurality of frame segments with respect to a locating surface on which the bed has been located, the rotation of the plurality of frame segments being achieved through one or more actuators.

17. A method for utilizing a bed for therapeutic and recreational applications, the bed comprising:
a frame structure,
a mattress provided on the frame structure of the bed,
a plurality of Light Emitting Diodes configured to emit electromagnetic radiation, an infrared heater assembly provided within the frame structure, the infrared heater assembly including a plurality of flexible heating elements connected with a power source, a plurality of temperature sensors provided at a plurality of locations on the frame structure and the mattress in order to generate signals in correlation with temperature recreational applications, the bed values at the plurality of locations, wherein the frame structure includes a plurality of frame segments adapted to rotate to respective predetermined angles in order to lift or recline the plurality of frame segments with respect to a locating surface on which the bed has been located, the rotation of the plurality of frame segments being achieved through one or more actuators; and wherein the mattress is made from at least partially transparent material and includes a fluid that is at least partially transparent, the method comprising steps of:

regulating electrical power being supplied to the one or more actuators in order to enable rotation of the plurality of frame segments, receiving the signals from the plurality of temperature sensors, determining the temperature values from the signals received from the plurality of temperature sensors, regulating electrical power being supplied to the infrared heater and the plurality of LEDs in correlation with the determined temperature values, and regulating emission characteristics of the electromagnetic radiation emitted by the plurality of LEDs.

18. A bed for therapeutic and recreational applications, the bed comprising:

a frame structure, a mattress provided on the frame structure of the bed, a plurality of Light Emitting Diodes (LEDs) configured to emit electromagnetic radiation, an infrared heater assembly provided within the mattress, the infrared heater assembly including a plurality of flexible heating elements connected with a power source, a plurality of temperature sensors provided at a plurality of locations on the frame structure and the mattress in order to generate signals in correlation with temperature values at the plurality of locations, wherein the frame structure includes a plurality of frame segments adapted to rotate to respective predetermined angles, in order to lift or recline, with respect to a locating surface on which the bed has been located, the rotation of the plurality of frame segments being achieved through one or more actuators, and wherein the mattress is made from at least partially transparent material and includes a fluid that is at least partially transparent.

19. The bed as claimed in claim 18, wherein the plurality of flexible heating elements are adapted to align with superficial veins of a body of a user.

* * * * *